US012788992B2

(12) United States Patent
Dawoud et al.

(10) Patent No.: US 12,788,992 B2
(45) Date of Patent: Nov. 10, 2026

(54) METHOD AND DEVICE FOR DISCRIMINATING MONOMORPHIC TACHYCARDIA AND OVERSENSING USING SIMILARITY AND CHARACTERISTICS OF ECG RHYTHMS

(71) Applicant: Pacesetter, Inc., Sylmar, CA (US)

(72) Inventors: Fady Dawoud, Studio City, CA (US); Fujian Qu, San Jose, CA (US); Wenwen Li, Porter Ranch, CA (US); Mark Sprowls, Sylmar, CA (US); Laukik Nagawekar, Sylmar, CA (US); Jennifer Lecocq Rhude, Carbondale, IL (US); Kevin J. Davis, Thousand Oaks, CA (US); Luke C. McSpadden, Los Angeles, CA (US)

(73) Assignee: Pacesetter, Inc., Sylmar (CA)

( * ) Notice: Subject to any disclaimer, the term of this patent is extended or adjusted under 35 U.S.C. 154(b) by 281 days.

(21) Appl. No.: 18/524,097

(22) Filed: Nov. 30, 2023

(65) Prior Publication Data

US 2024/0189603 A1 Jun. 13, 2024

Related U.S. Application Data

(60) Provisional application No. 63/386,525, filed on Dec. 8, 2022.

(51) Int. Cl.

| | |
|---|---|
| ***A61N 1/365*** | (2006.01) |
| ***A61B 5/352*** | (2021.01) |
| ***A61B 5/366*** | (2021.01) |

(52) U.S. Cl.

CPC .............. *A61N 1/365* (2013.01); *A61B 5/352* (2021.01); *A61B 5/366* (2021.01)

(58) Field of Classification Search

CPC ........ A61N 1/365; A61B 5/352; A61B 5/366; A61B 5/35

See application file for complete search history.

(56) References Cited

U.S. PATENT DOCUMENTS

| | | |
|---|---|---|
| 7,826,893 B2 | 11/2010 | Cao et al. |
| 8,538,524 B2 | 9/2013 | Rosenberg et al. |

(Continued)

FOREIGN PATENT DOCUMENTS

| | | | |
|---|---|---|---|
| AU | 2010201351 A1 * | 4/2010 | A61N 1/3621 |
| WO | WO-2016003557 A1 * | 1/2016 | A61B 5/7221 |
| WO | WO-2024089501 A1 * | 5/2024 | A61N 1/37247 |

*Primary Examiner* — Carl H Layno

*Assistant Examiner* — Heidi A Hilsmier

(74) *Attorney, Agent, or Firm* — Dean D. Small; Carroll, Hoette & Butscher, LLC

(57) ABSTRACT

Methods, devices, and program products are provided under control of one or more processors within an implantable medical device (IMD) that senses far field (FF) signals between a combination of electrodes coupled to the IMD. Correlation scores are determined by comparing the FF signals associated with a number of beats to a template. The correlation scores of the number of beats are compared to a correlation threshold, and correlation variability scores are determined for the number of beats. Shock delivery, by a pulse generator within the IMD, is postponed in response to i) a first number of beats within the number of beats having the correlation scores that are less than the correlation threshold, and ii) a second number of beats within the number of beats having correlation variability scores that are less than a correlation variability threshold.

11 Claims, 15 Drawing Sheets

(56) References Cited

U.S. PATENT DOCUMENTS

| | | | | |
|---|---|---|---|---|
| 9,220,434 | B2 | 12/2015 | Snell et al. | |
| 9,421,061 | B2 * | 8/2016 | Ben Zriham | A61B 5/283 |
| 10,350,415 | B2 | 7/2019 | Kaiser | |
| 11,383,089 | B2 | 7/2022 | Rhude | |
| 11,931,585 | B2 * | 3/2024 | Mischler | A61B 5/686 |
| 12,337,185 | B1 * | 6/2025 | Sullivan | A61B 5/024 |
| 2012/0108994 | A1 * | 5/2012 | Patel | A61B 5/322 600/515 |
| 2016/0121127 | A1 * | 5/2016 | Klimovitch | A61N 1/37288 607/32 |
| 2017/0043173 | A1 * | 2/2017 | Sharma | A61N 1/3925 |
| 2017/0209696 | A1 | 7/2017 | Kaiser | |
| 2019/0336767 | A1 * | 11/2019 | Klepfer | A61N 1/3987 |
| 2020/0170532 | A1 * | 6/2020 | Zhang | A61N 1/3925 |

* cited by examiner

METHOD AND DEVICE FOR DISCRIMINATING MONOMORPHIC TACHYCARDIA AND OVERSENSING USING SIMILARITY AND CHARACTERISTICS OF ECG RHYTHMS

CROSS-REFERENCE TO RELATED APPLICATIONS

This application claims priority to U.S. Provisional Patent Application No. 63/386,525, filed 8 Dec. 2022, entitled "METHOD AND DEVICE FOR DISCRIMINATING MONOMORPHIC TACHYCARDIA AND OVERSENSING USING SIMILARITY AND CHARACTERISTICS OF ECG RHYTHMS", the subject matter of which is incorporated herein by reference in its entirety.

BACKGROUND

Embodiments of the present disclosure generally relate to methods and devices for discriminating monomorphic ventricular tachycardia from polymorphic ventricular tachycardia, as well as determining oversensing conditions using similarity and characteristics of ECG rhythms to inhibit unnecessary device tachycardia therapy.

Implantable medical devices (IMD) provide various types of electrical stimulation, such as in connection with delivering pacing therapy and/or high-energy defibrillation shock to one or more select chambers of the heart. An IMD may provide both unipolar and bipolar pacing and/or sensing configurations. In the unipolar configuration, the pacing pulses are applied (or responses are sensed) between an electrode carried by the lead and a case (e.g., can) of the pulse generator or a coil electrode of another lead within the heart. In the bipolar configuration, the pacing pulses are applied (or responses are sensed) between a pair of electrodes carried by the same lead. IMDs may implement single-chamber, dual-chamber, or triple-chamber functionality.

Prior to delivering therapy, it is important to determine if treatment is required, when treatments should be delivered and the appropriate type of treatment. The first step is to determine the origin of the tachycardia. A tachycardia arising in the atrium is not a candidate for treatment with traditional ICD therapies as they are not life-threatening, whereas tachycardias arising in the ventricles, such as ventricular fibrillation (VF) or ventricular tachycardia (VT), are often more serious since they can be fatal if untreated. Among the forms of VT, monomorphic VT (MVT) can often be hemodynamically tolerated for an extended period of time due to the heart still generating effective contraction and have a likelihood of self-terminating while polymorphic VT (PVT) is less likely to provide sufficient hemodynamic support and more likely to persist or degenerate to VF. Therefore, PVT/VF can be a life-threatening condition and is generally treated immediately by delivering a high-energy defibrillation shock, referred to herein as "shock therapy delivery". MVT, though not immediately life threatening, is a serious condition and can be first treated by delaying any therapy to allow for self-termination or with lower energy ventricular anti-tachycardia pacing therapy prior to attempting painful shock therapy, thereby reducing the delivery of defibrillation shocks and the subsequent electrical shock to cardiac tissue and the subject's psychological trauma. A supraventricular tachycardia (SVT) has an origin that is above the ventricles, but which is conducted to the ventricles resulting in unacceptably rapid ventricular rate. The true underlying arrhythmia of SVT may be, e.g., atrial fibrillation (AF), sinus tachycardia (ST), ectopic atrial tachycardia, atrial reentry tachycardia, atrioventricular (AV) nodal reentry tachycardia or atrial flutter. Failure to distinguish SVT from VT can result in delivery of inappropriate therapy. Depending upon the capabilities of the ICD, inappropriate therapy might involve delivery of unnecessary and painful electrical shocks to the heart or improper delivery of anti-tachycardia pacing (ATP) which in itself might unnecessarily induce ventricular tachycardia.

Currently, transvenous ICD (TV-ICD) devices (e.g., a type of IMD) use a morphology similarity algorithm (e.g., far field morphology (FFM)) to discriminate between SVT and VT. Morphologic discrimination procedures typically detect sensed QRS beats during normal sinus rhythm and record a morphology template that represents the expected QRS complex during normal sinus rhythm or atrial pacing. If a tachycardia is detected (e.g., based on the ventricular rate exceeding a VT threshold), the morphology discriminator compares the morphological profile of sensed QRS beats to the previously stored template and makes the determination about the type of arrhythmia (e.g., SVT vs. VT). For example, if there is a substantial match, the tachycardia is deemed SVT and no ventricular shock or ATP therapy is delivered.

On the other hand, if the comparison to the template is an insubstantial match, the tachycardia is deemed to be MVT or PVT/VF. In MVT scenarios, delaying shocking therapy delivery can be clinically warranted (in the absence of ATP therapy) to provide a short period of time for arrhythmia to self-terminate. Accurate identification of scenarios of MVT is crucial in order to provide prompt defibrillation in non-MVT scenarios (e.g., PVT or VF) while preventing unnecessary shock therapy delivery.

SUMMARY

In accordance with embodiments herein, a method is provided, under control of one or more processors within an implantable medical device (IMD), the IMD including sensing circuitry and a pulse generator. The method utilizes the sensing circuitry to sense far field (FF) signals between a combination of electrodes coupled to the IMD and determine correlation scores by comparing the FF signals associated with a number of beats to a template. The method compares the correlation scores of the number of beats to a correlation variability threshold and determines correlation variability scores for the number of beats. The method postpones shock delivery, by the pulse generator, in response to i) a first number of beats within the number of beats having the correlation scores that are less than the correlation threshold, and ii) a second number of beats within the number of beats having correlation variability scores that are less than the correlation variability threshold.

Optionally, wherein the determining and comparing the correlation scores and the determining the correlation variability scores of the method are performed in response to a heart rate level exceeding a threshold. Optionally, the method further comprising wherein the determining the correlation variability threshold further comprises determining a mean or median based on the correlation scores of the number of beats, and comparing an absolute difference of each of the number of beats to the mean or median to determine the number of beats having stable correlation scores. Optionally, wherein the correlation variability threshold is i) an absolute value or ii) a percentage of a mean of the correlation scores.

Optionally, the method further comprises determining an absolute mean of QRS-wave peak amplitudes of the number of beats, determining peak amplitude stability score associated with a third number of beats within the number of beats, wherein the peak amplitude stability score includes a relative absolute deviation from the absolute mean of the QRS-wave peak amplitudes of the number of beats, and wherein the postponing shock delivery is performed further in response to i) determining that the absolute mean of the QRS-wave peak amplitudes of the number of beats is higher than a QRS-wave peak amplitude of the template multiplied by a factor, and ii) determining that the third number of beats have peak amplitude stability scores of less than a predetermined amplitude.

Optionally, the method further comprising determining RR intervals associated with the number of beats, determining a mean or median associated with the RR intervals, comparing a relative absolute difference of the RR intervals to the mean or median associated with the RR intervals, and wherein the postponing shock delivery is performed further in response to determining that a fourth number of beats within the number of beats have a relative absolute difference to the mean or median that is less than a heart rate stability threshold.

Optionally, the method further comprising determining durations of QRS complexes associated with the number of beats, determining a mean associated with the durations of the QRS complexes, and wherein the postponing shock delivery is performed further in response to i) determining that a fifth number of beats within the number of beats have durations of the QRS complexes that are equal to a duration of a QRS complex associated with the template or greater than a first predetermined time duration, and ii) determining that a sixth number of beats within the number of beats have an absolute deviation from the mean associated with the durations of the QRS complexes that is less than a second predetermined time duration.

Optionally, the method declares a shockable diagnosis in response to i) the first number of beats within the number of beats having the correlation scores that are less than the correlation variability threshold, or ii) the second number of beats within the number of beats having the correlation variability scores that are greater than the correlation variability threshold. Optionally, wherein the template is representative of a sinus QRS rhythm or atrial pacing, and is acquired using the combination of electrodes.

Optionally, the method further comprising comparing the correlation scores of the number of beats to a first sinus template correlation condition, and in response to the comparison indicating that the number of beats indicate a VT, comparing the correlation scores of the number of beats to a second sinus template correlation condition, wherein the second sinus template correlation condition is a reduced level of correlation compared to the first sinus template correlation condition.

In accordance with embodiments herein, a system is provided comprising electrodes; an implantable medical device (IMD) coupled to the electrodes, the IMD including sensing circuitry, the IMD configured to sense far field (FF) signals, utilizing the sensing circuitry, between the electrodes; memory to store the FF signals and to store program instructions, the memory further storing a template associated with a set of the electrodes; and a processor. The processor, when executing the program instructions, is configured to declare an MVT diagnosis based on i) a comparison of correlation scores of a plurality of recent beats to a correlation threshold, wherein the recent beats are based on the FF signals sensed between the set of the electrodes, wherein the correlation scores are based on a comparison between the plurality of recent beats and the template stored in the memory and ii) a variability of the correlation scores of the plurality of recent beats being less than a correlation variability threshold.

Optionally, the IMD further comprises a pulse generator, and the processor may be further configured to postpone shock delivery in response to the processor declaring the MVT diagnosis. Optionally, in response to the processor declaring a second MVT diagnosis within a predetermined time of the MVT diagnosis, the processor is further configured to postpone shock delivery a second time. Optionally, the processor is further configured to declare the MVT diagnosis based on a comparison of R-wave peak amplitudes of the plurality of recent beats to an R-wave peak amplitude associated with the template. Optionally, the processor is further configured to declare the MVT diagnosis based on a heart rate stability associated with the plurality of recent beats.

Optionally, the processor is further configured to declare the MVT diagnosis based on i) a comparison of durations of QRS complexes associated with the plurality of recent beats to a duration of a QRS complex associated with the template and ii) a stability of the durations of the QRS complexes associated with the plurality of recent beats. Optionally, wherein the IMD is further configured to sense the FF signals, utilizing the sensing circuitry, between a second set of the electrodes, wherein at least one of the electrodes within the second set of the electrodes is different from one of the electrodes within the set of the electrodes, and wherein the memory is further configured to store a second template associated with the second set of the electrodes.

In accordance with embodiments herein, a system is provided comprising implantable electrodes; an implantable medical device (IMD) coupled to the electrodes, the IMD including sensing circuitry and a pulse generator, the IMD configured to sense far field (FF) signals, utilizing the sensing circuitry, between the electrodes; memory to store the FF signals and to store program instructions, the memory further storing a template associated with a set of the electrodes; and a processor. The processor, when executing the program instructions, is configured to postpone shock delivery, by the pulse generator, based on i) a determination that correlation scores of a plurality of recent beats form more than one cluster, wherein the recent beats are associated with the FF signals sensed between the set of the electrodes, 2) a determination that amplitudes of sensed R-waves within the plurality of recent beats form more than one cluster, 3) a determination that RR intervals form more than one cluster, or 4) a determination that sense-to-peak durations form more than one cluster. Optionally, the processor, in response to determining that the correlation scores of the plurality of recent beats form one cluster, is further configured to declare that oversensing is not occurring. Optionally, the oversensing is i) P-wave oversensing, ii) T-wave oversensing, or iii) QRS-wave oversensing.

In accordance with embodiments herein, a system is provided comprising electrodes and an implantable medical device (IMD) coupled to the electrodes. The IMD includes sensing circuitry and a pulse generator, and is configured to sense far field (FF) signals and near field (NF) signals, utilizing the sensing circuitry, between the electrodes. The system also comprises a memory to store the FF signals and the NF signals and to store program instructions, and a processor that, when executing the program instructions, is configured to postpone shock delivery, by the pulse generator, based on the FF signals or the NF signals. The postponing the shock delivery is further based on i) a comparison of a mean of absolute peak amplitudes of QRS-wave peaks of a plurality of recent beats to a first voltage threshold; ii) a comparison of absolute peak amplitudes of the QRS-wave peaks of the plurality of recent beats to a second voltage threshold; iii) a comparison of a mean of an absolute difference of beat-to-beat peak amplitudes of the QRS-wave peaks of the plurality of recent beats to a third voltage threshold; or iv) a comparison of an absolute difference of the beat-to-beat peak amplitudes of the QRS-wave peaks of the plurality of recent beats to an amplitude stability threshold.

Optionally, the postponing the shock delivery is further based on both the FF signals and the NF signals. Optionally, the postponing the shock delivery is further based on i) a comparison of beat-to-beat RR intervals of the plurality of recent beats to a heart rate threshold; ii) a comparison of a range of RR intervals to a heart rate range stability threshold, the range of the RR intervals based on the plurality of recent beats and excluding at least one of a highest value and a lowest value; iii) a comparison of a largest absolute beat-to-beat interval difference of the beat-to-beat RR intervals of the plurality of recent beats to the heart rate range stability threshold; or iv) a determination of a percentage of the RR intervals, of the plurality of recent beats, with an absolute difference less than a heart stability threshold, wherein the percentage is compared to a predetermined percentage.

DETAILED DESCRIPTION

Figure 1:
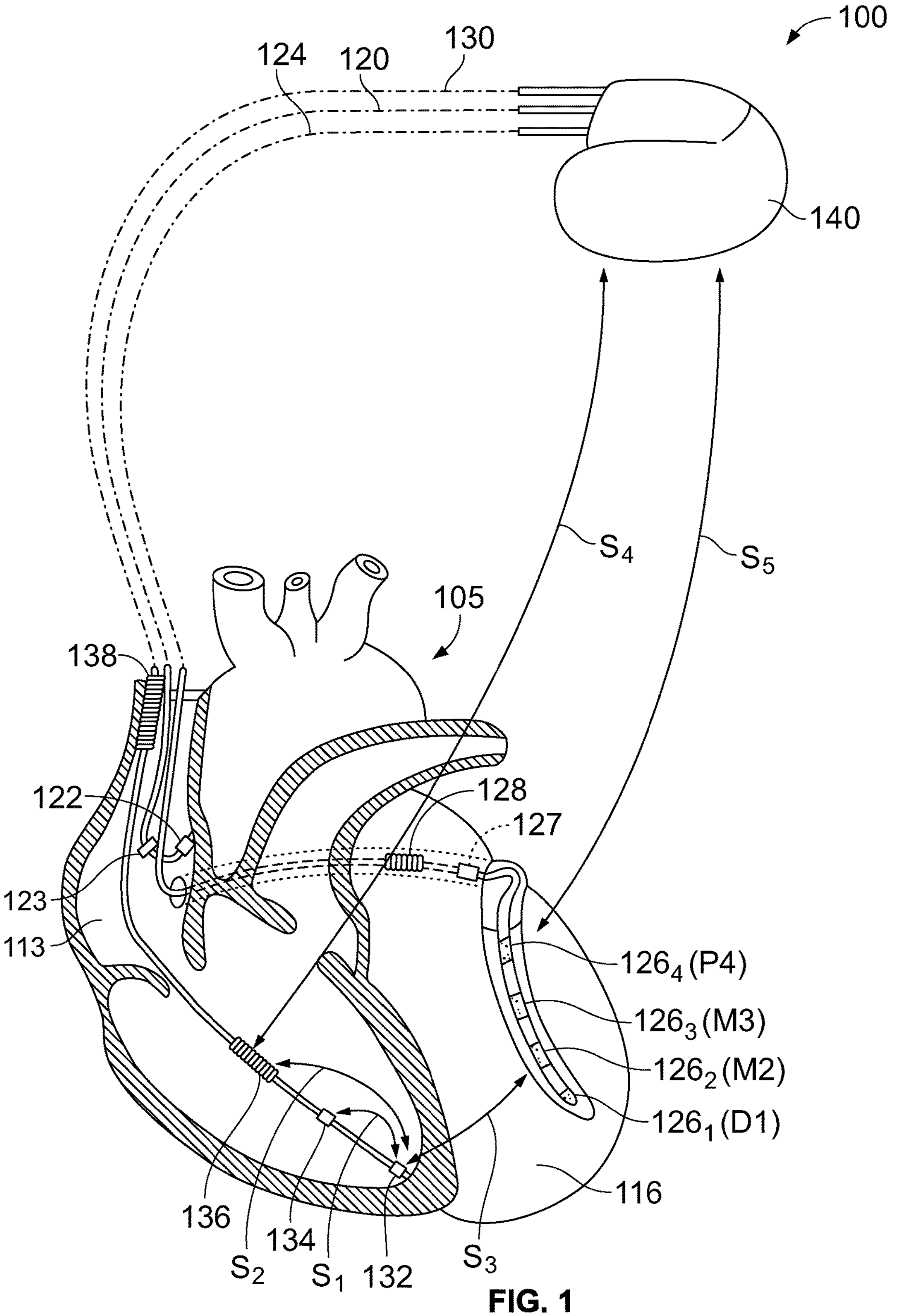
FIG. 1 illustrates an IMD coupled to a heart in a patient and implemented in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "oversensing" shall mean, as used throughout, referring to an operation by an IMD that occurs when electrical signals are inappropriately recognized, by an IMD, as native cardiac activity. The inappropriate signals may result from large R-waves, P-waves, T-waves, skeletal muscle activity or lead contact problems.

The terms "monomorphic ventricular tachycardia" and "MVT" shall mean a type of irregular heart rhythm (arrhythmia) that happens when the lower chambers of the heart (e.g., ventricles) beat at a fast pace that exceeds a threshold.

MVT demonstrates a stable QRS morphology from beat-to-beat, stable heart rate, stable QRS duration and similar or larger peak QRS-wave amplitude compared to sinus QRS-wave.

The terms "polymorphic ventricular tachycardia" and "PVT" shall mean a type of irregular heart rhythm (arrhythmia) that happens when the lower chambers of the heart (e.g., ventricles) beat at a fast pace that exceeds a threshold. PVT demonstrates a changing or multiform QRS variance from beat-to-beat. PVT/VF has less stable morphology, less stable and faster heart rate, less stable QRS duration and smaller peak ECG amplitude compared to MVT and sinus QRS-waves.

The terms "supraventricular tachycardia" and "SVT" shall mean a type of irregular heart rhythm (arrhythmia) that originates from above the ventricles.

The terms "cluster" and "cluster pattern" shall mean a group that has some similarity in level or score. For example, the level or score within a cluster does not have a lot of variance or deviation from a mean value, and individual values remain consistently around or about a same value or mean value.

The term "shock therapy delivery" shall mean a high-voltage shock and/or a medium-voltage shock. A high-voltage shock refers to defibrillation stimulus delivered at an energy level sufficient to terminate a defibrillation episode in a heart, wherein the energy level is defined in Joules (J) to be 40J or more and/or the energy level is defined in terms of voltage (V) to be 750V or more. A medium-voltage shock refers to defibrillation stimulus delivered at an energy level sufficient to terminate a defibrillation episode in a heart, wherein the energy level is defined in Joules, pulse width, and/or maximum charge voltage. An MV shock from an implantable medical device (IMD) with a transvenous lead can have a different maximum energy and/or charge voltage than an MV shock from a subcutaneous IMD with a subcutaneous lead. In connection with an IMD having a transvenous lead, the terms medium voltage shock and MV shock refer to defibrillation stimulation that has an energy level that is no more than 25 J, and more preferably 15 J-25 J and/or has a maximum voltage of no more than 500 V, preferably between 100 V-475 V and more preferably between 400 V-475 V. Shock therapy delivery can equally be delivered by a subcutaneous implantable cardiac device (SICD), utilizing far-field signal(s) among electrodes/coils below skin and the can of the device.

The scenarios can compare measured and projected values to limits, ranges, and the like. Further, the terms "about", "around", and/or "approximately" as used in this association shall mean that the values indicated for comparison are not limited and are contemplated to include ranges such as +/−1%, +/−2%, +/−3%, +/−4%, +/−5%, +/−10%, +/−15%, +/−20%, etc., of the value.

In accordance with embodiments herein, methods and systems are described that analyze far field (FF) signals to determine whether a monomorphic VT is occurring and/or to determine whether oversensing is occurring. Embodiments herein differentiate between an MVT and a PVT diagnosis to facilitate the selection of an appropriate corresponding therapy. Embodiments herein compare characteristics of interest from the FF signal to one or more stored template(s) representative of normal sinus rhythm and/or atrial pacing to determine correlation scores. For example, templates can be acquired at different rates to assist with rate-related aberrancy that may occur with AF. The correlation scores of a number of beats are compared to one or more thresholds to determine whether the signal is indicative of an MVT or PVT. Further, characteristics of the FF signal, such as amplitude stability over time, heart rate stability over time, and QRS duration stability over time can be compared to thresholds to determine whether the signal is indicative of an MVT or PVT. Embodiments herein can further utilize characteristics of interest from the FF signal to compare beats to determine whether oversensing of P-waves and/or T-waves is occurring. The correlation scores, amplitudes, RR intervals, and sense-to-peak durations can be evaluated to determine whether they form more than one cluster. If more than one cluster is identified, oversensing is occurring.

Embodiments may be implemented in connection with one or more implantable medical devices (IMDs) and/or implantable cardiac devices. Non-limiting examples of IMDs include one or more of subcutaneous devices, transvenous devices, neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker, and the like. For example, the IMD may include one or more structural and/or functional aspects of the device(s) described in U.S. Pat. No. 9,333,351 "Neurostimulation Method and System to Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Patent 9,216,285 "Leadless Implantable Medical Device Having Removable and Fixed Components" and U.S. Patent 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method and System for Identifying a Potential Lead Failure in an Implantable Medical Device" and U.S. Pat. No. 9,232,485 "System And Method For Selectively Communicating With An Implantable Medical Device", which are hereby incorporated by reference.

Embodiments herein may be implemented in connection with the concepts described in the following patents and applications, all of which are expressly incorporated in their entirety by reference: U.S. Pat. No. 8,538,524, titled "Systems and Methods for Detecting Far-Field Oversensing based on Signals Sensed by the Proximal Electrode of a Multipolar LV Lead" having an issue date of Sep. 17, 2013; U.S. Pat. No. 11,383,089, titled "Method and Device Utilizing Far Field Signals to Identify and Treat Under-Detected Arrythmias" having an issue date of Jul. 12, 2022; and U.S. Pat. No. 9,220,434, titled "Systems and Methods for Selectively Updating Cardiac Morphology Discrimination Templates for use with Implantable Medical Devices" having an issue date of Dec. 29, 2015; U.S. Pat. No. 10,350,415, titled "Systems and methods to optimize anti-tachycardial pacing (ATP)" having an issue date of Jul. 16, 2019; and US Patent Application 2017/0209696, titled "Systems and methods to improve anti-tachycardial pacing (atp) algorithms", published Jul. 27, 2017. The patents, applications and publications listed herein are expressly incorporated by reference in their entireties.

FIG. 1 illustrates an IMD 100 coupled to a heart in a patient and implemented in accordance with one embodiment. The IMD 100 can be a subcutaneous IMD/ICD, a transvenous IMD/ICD, or other implantable cardiac monitor and/or therapy delivery device known in the art. The IMD 100 may communicate with an external device such as a programmer, an external defibrillator, a workstation, a portable computer, a personal digital assistant, a cell phone, a bedside monitor, and the like. The IMD 100 may represent a cardiac monitoring device, pacemaker, cardioverter, cardiac rhythm management device, defibrillator, neurostimulator, leadless monitoring device, leadless pacemaker, and the like, implemented in accordance with one embodiment of the present invention. The IMD 100 can be positioned subcutaneously (e.g., implanted under the skin below the armpit), transvenously (e.g., implanted under the skin underneath the collar bone), or positioned in another location within the body. The IMD 100 may be a single-chamber or dual-chamber stimulation device capable of treating both fast and slow arrhythmias with stimulation therapy, including cardioversion, defibrillation, and pacing stimulation, including CRT. Optionally, the IMD 100 may be configured for multi-site left ventricular (MSLV) pacing, which provides pacing pulses at more than one site within the LV chamber each pacing cycle. To provide atrial chamber pacing stimulation and sensing, IMD 100 is shown in electrical communication with a heart 105 by way of a right atrial (RA) lead 120 having an atrial tip electrode 122 and an RA ring electrode 123 implanted in the atrial appendage 113. A right ventricular (RV) lead 130 has a ventricular tip electrode 132, an RV ring electrode 134, an RV coil electrode 136, and a superior vena cava (SVC) coil electrode 138. The RV lead 130 is transvenously inserted into the heart 105 so as to place the RV coil electrode 136 in the RV apex, and the SVC coil electrode 138 in the superior vena cava.

To sense left atrial and ventricular cardiac signals and to provide left ventricle 116 (e.g., left chamber) pacing therapy, IMD 100 is coupled to a multi-pole left ventricular (LV) lead 124 designed for placement in the "CS region." As used herein, the phrase "CS region" refers to the venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus. In an embodiment, an LV lead 124 is designed to receive atrial and ventricular cardiac signals and to deliver left ventricular pacing therapy using a set of multiple LV electrodes 126 that includes electrodes $\mathbf{126}_1$, $\mathbf{126}_2$, $\mathbf{126}_3$, and $\mathbf{126}_4$(thereby providing a multipolar or multi-pole lead). The LV lead 124 also may deliver left atrial pacing therapy using at least a left atrial (LA) ring electrode 127 and shocking therapy using at least an LA coil electrode 128. In alternate embodiments, the LV lead 124 includes the LV electrodes $\mathbf{126}_1$, $\mathbf{126}_2$, $\mathbf{126}_3$, and $\mathbf{126}_4$, but does not include the LA electrodes 127 and 128. Although three leads 120, 124, and 130 are shown in FIG. 1, fewer or additional leads with various numbers of pacing, sensing, and/or shocking electrodes may optionally be used. The LV electrodes $\mathbf{126}_1$, $\mathbf{126}_2$, $\mathbf{126}_3$, and $\mathbf{126}_4$may be referred to respectively as electrodes D1, M2, M3, and P4 (where "D" stands for "distal", "M" stands for "middle", and "P" stands from "proximal", and the numbers are arranged from most distal to most proximal, as shown in FIG. 1). Optionally, more or fewer LV electrodes may be provided on the lead 124 than the four LV electrodes D1, M2, M3, and P4.

While FIG. 1 illustrates multiple leads provided within the heart, it is understood that only one or more of the leads 124, 120 and 130 may be utilized and the other leads 124, 120 and 130 may be removed. For example, the lead 120 and the lead 124 may be removed, leaving only the lead 130 to support right side ventricular pacing and sensing.

In a pacing vector or a sensing vector, each LV electrode 126 may be controlled to function as a cathode (negative electrode). Pacing pulses may be directionally provided between electrodes to define a pacing vector. Optionally, combinations of LV electrodes 126 are paired with one another to operate as a common virtual electrode, such as a common virtual cathode, when delivering pacing therapies. The electrodes that define the pacing vectors may be electrodes in the heart 105 or located externally to the heart 105 (e.g., on a housing/case/CAN 140 of the device). For example, the housing/case 140 may be referred to as the CAN 140 and function as an anode in unipolar pacing and/or sensing vectors. The LV electrodes 126 may be used to provide various different vectors. Some of the vectors are intraventricular LV vectors (e.g., vectors between two of the LV electrodes 126), while other vectors are interventricular vectors (e.g., vectors between an LV electrode 126 and the RV coil 136 or another electrode remote from the left ventricle 116).

Near field (NF) and far field (FF) sensing vectors collect near field and far field signals. FIG. 1 illustrates examples of different sensing vectors between different combinations of electrodes. The sensing vectors are divided into near field sensing vectors S1-S3 and far field sensing vectors S4-S5. The near field sensing vectors S1-S3 sense near field signals, while the far field sensing vectors sense far field signals. For example, NF sensing vector S1 is between RV tip and ring electrodes 132, 134, NF sensing vector S2 is between RV tip and coil electrodes 132, 136, and NF sensing vector S3 is between RV tip electrode 132 and one or more LV electrodes 126. The FF sensing vector S4 is between the RV coil electrode 136 and the CAN electrode formed by the housing 140 of the IMD. Additionally or alternatively, the FF sensing vector S5 may be utilized between the RV tip electrode 132 and the CAN electrode formed by the housing 140 of the IMD. In some embodiments, one or more additional FF sensing vectors can be formed between another electrode and the CAN electrode.

Optionally, the sensing vectors S1, S2 and S4 may be provided in a configuration in which the RV lead 130 is utilized alone, while the leads 120, 124 are omitted entirely. Additionally or alternatively, NF sensing vector S3 and FF sensing vector S5 may be utilized in a configuration with RV lead 130 and LV lead 124, with or without the inclusion of the RA lead 120. Below is a list of example bipolar sensing vectors with LV cathodes that may be used for sensing using the LV electrodes D1, M2, M3, and P4. In the following list, the electrode to the left of the arrow is the cathode, and the electrode to the right of the arrow is the anode: D1→M2; D1→P4; M2→P4; M3→M2; M3→P4; and P4→M2.

Figure 2A:
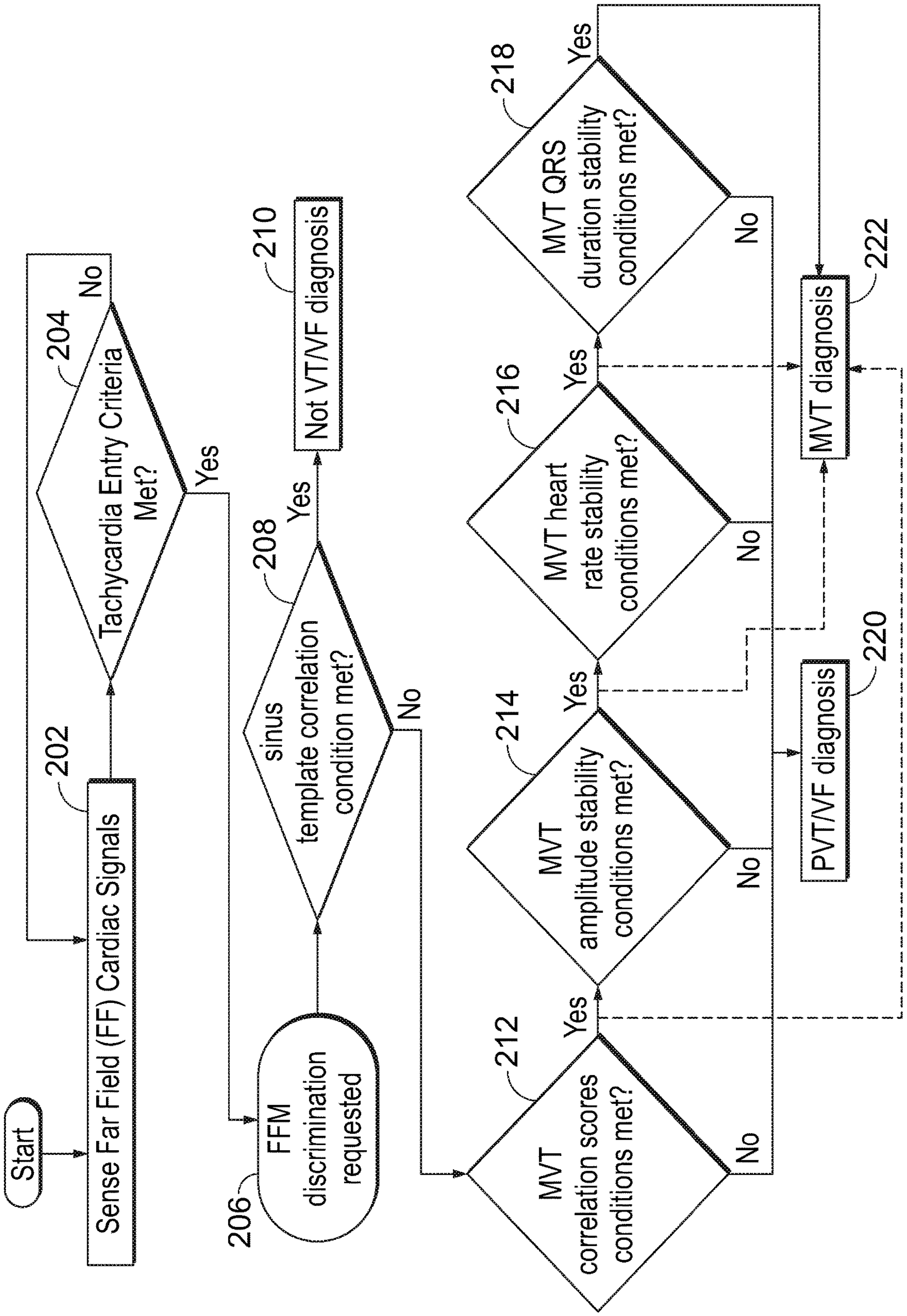
FIG. 2A illustrates a process for utilizing far field (FF) signals to discriminate between supraventricular tachycardia (SVT), monomorphic ventricular tachycardia (MVT) and polymorphic ventricular tachycardia or ventricular fibrillation (PVT/VF) in accordance with embodiments herein.

FIG. 2A illustrates a process for utilizing FF signals to discriminate between SVT, MVT and PVT/VF in accordance with embodiments herein. The operations of FIG. 2A may be implemented by hardware, firmware, circuitry and/or one or more processors housed partially and/or entirely within the IMD 100, a local external device, remote server or more generally within a healthcare system. Optionally, the operations of FIG. 2A may be partially implemented by an IMD 100 and partially implemented by a local external device, remote server or more generally within a healthcare system. For example, the IMD 100 includes IMD memory and one or more IMD processors, while each of the external devices/systems (e.g., local, remote, or anywhere within the healthcare system) include external device memory and one or more external device processors. In some embodiments, the discriminator methods described herein can all or partly be performed by firmware, software, hardware, etc., on a beat-by-beat basis or on-demand using buffered data. Further, the IMD 100 can be a subcutaneous IMD/ICD, a transvenous IMD/ICD, or other implantable cardiac monitor known in the art.

Under control of one or more processors within an IMD 100, at 202, sensors sense far field (FF) signals between first and second combinations of electrodes coupled to the IMD 100 and/or to an external device. By way of example, an IMD 100 may sense FF and/or NF signals and internally and automatically implement the operations of FIG. 2A, FIG. 2B, FIG. 4C and/or FIG. 5C, discriminating between arrhythmias and oversensing conditions, and based thereon, postpone shock delivery, declare shock delivery postponement, declare an MVT diagnosis, inhibit shock therapy delivery, deliver the appropriate therapy (e.g., anti-tachycardia pacing, shock therapy delivery, etc.), and/or adjust sensing and/or therapy parameters. Additionally, or alternatively, the IMD 100 may sense the FF signals, wirelessly convey the FF signals in real time to an external device, where the external device performs all or a portion of the operations of FIG. 2A, FIG. 2B, FIG. 4C and/or FIG. 5C discussed herein. The external device discriminates between arrhythmias and oversensing conditions, and based thereon, the external device directs the IMD 100 to postpone shock delivery and/or declare shock delivery postponement, declare an MVT diagnosis, inhibit shock therapy delivery, deliver the appropriate therapy (e.g., anti-tachycardia pacing, shock therapy delivery, etc.), and/or adjust sensing and/or therapy parameters. Although some of the embodiments herein are primarily discussed with respect to acquiring and processing FF signals, it should be understood that NF signals may be used instead or FF signals, and/or a combination of NF and FF signals.

In accordance with embodiments herein, FF signals may be sensed at 202 over a desired number of cardiac events/beats and/or may be continuously sensed for analysis. At 204, one or more processors determine whether tachycardia entry criteria are met. Tachycardia entry criteria can be met after a certain number of beats are sensed above a tachycardia rate therapy zone. For example, the one or more processors determine if a certain number of RR intervals<ventricular tachycardia (VT) zone RR interval cut-off. If the tachycardia entry criteria are not met, the process returns to 202. In some embodiments, the one or more processors can evaluate the beats (e.g., RR intervals) to monitor for fast beats that are sustained, such as for 20-30 or more beats, but the embodiment is not so limited. If the tachycardia entry criteria are met, the process passes to 206 and the one or more processors request far field morphology (FFM) discrimination.

At 208, the one or more processors compare a number (e.g., 10) of most recent sensed beats to a sinus QRS template to evaluate morphology similarity. It should be understood that more or less beats can be evaluated. Further, all, most, or some stored beats can be compared to the QRS template, and in other embodiments, beats can be compared to the QRS template as they are acquired. The one or more processors can align the sensed beats with the stored sinus QRS template using locations of peak R-waves and perform, for example, a one-shot cross-correlation to determine similarity between the sensed tachycardia beats and the stored sinus QRS template. When a predetermined number or percentage of beats (e.g., X out of Y beats) meet or exceed a similarity score, the rhythm is determined to be supraventricular (SVT) in origin (e.g., the source of the tachycardia is outside the ventricles) and thus not a shockable event. In some embodiments, if three out of ten beats have a similarity score greater than a threshold correlation score of 90 percent, the rhythm is determined to be SVT and the process passes to 210. Other treatment and/or analysis may be accomplished concerning the SVT rhythm.

In other embodiments, referring again to 208, multiple sinus template correlation conditions (e.g., multiple X out of Y conditions based on sinus template correlation to most recent beats) can be used to differentiate SVT vs VT/VF. In some cases, correlation scores can be high but may not exceed the threshold of a correlation condition for determining that the most recent beats indicate SVT. The one or more processors can compare correlation scores of the number of beats to a first sinus template correlation condition. For example, if the first sinus template correlation condition of 3 out 10 most recent beats with correlation score>0.9 fails (e.g., indicates VT/VF rather than SVT), the one or more processors can compare correlation scores of the number of beats to a second sinus template correlation condition. For example, if 5 out of 10 of the most recent beats have a correlation score>a second threshold correlation score that is lower, such as 0.85 (e.g., the second threshold correlation score is lower than a first correlation score associated with the first sinus template correlation condition), the second sinus template correlation condition, which has a reduced level of correlation in comparison with the first sinus template correlation condition, is met. If the second condition is met, the process can flow to 210, as the rhythm is determined to be SVT.

If the template threshold correlation score is not met at 208, the process determines, based on one or more conditions (e.g., condition sets wherein each set can include one or more conditions), whether to declare an MVT diagnosis or a PVT/VF diagnosis. For example, correlation scores (212), amplitude stability (214), heart rate stability (216), and QRS duration stability (218) can be evaluated consecutively, in any order, and/or simultaneously. Further, the MVT diagnosis (222) can be declared after one, two, three, or all four of the conditions are met. Therefore, it should be understood that after any one or more of the condition sets are not met, the process can declare a shockable diagnosis (e.g., PVT/VF diagnosis) (220), and in some cases, the one or more processors can initiate shock therapy delivery or other processing and/or sensing algorithms as are known in the art.

Figure 3A:
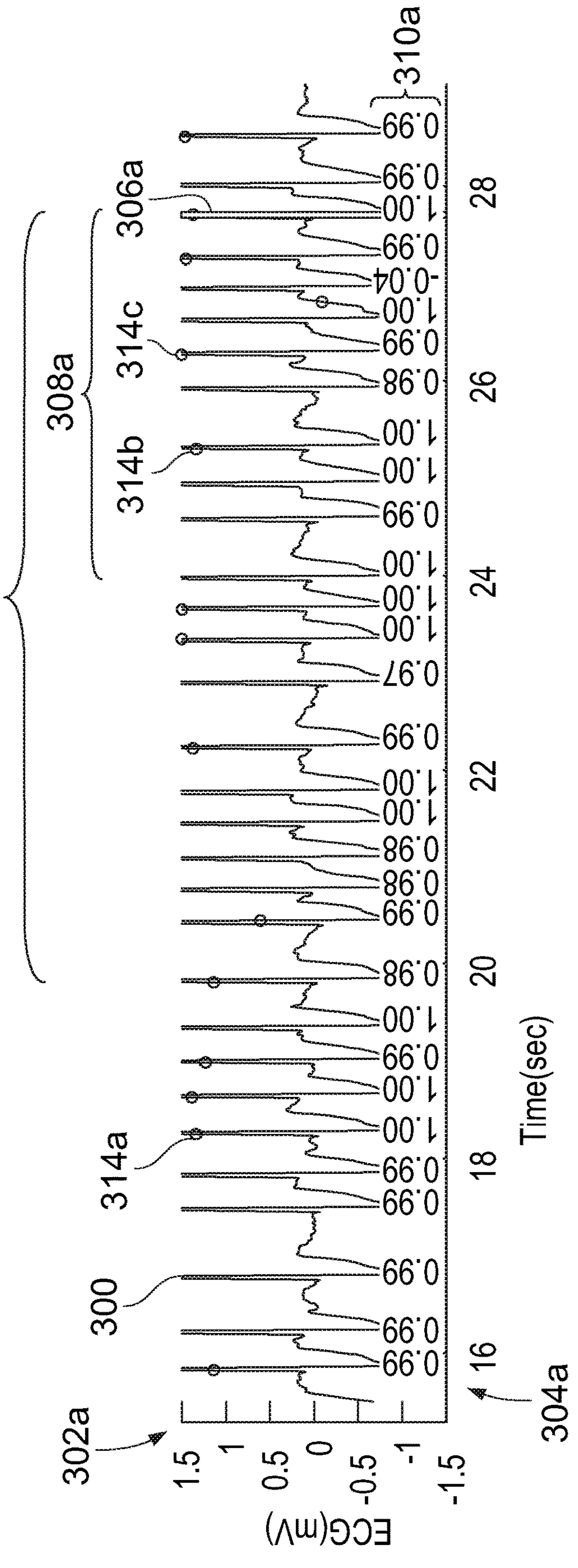
FIGS. 3A-3C illustrate example traces of SVT, MVT, and PVT/VF with correlation scores indicated for individual beats in accordance with embodiments herein.
Figure 3B:
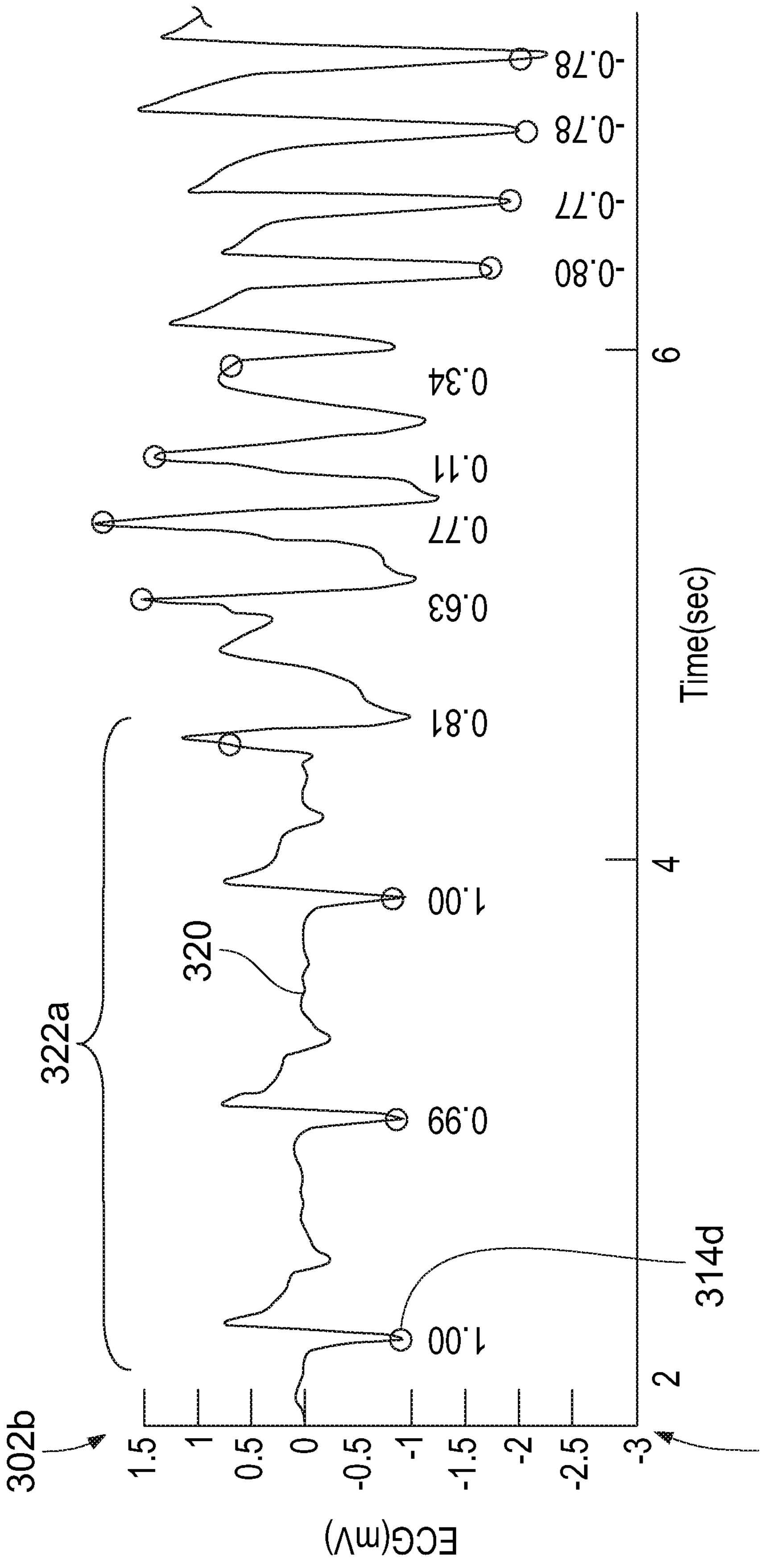
Figure 3B:
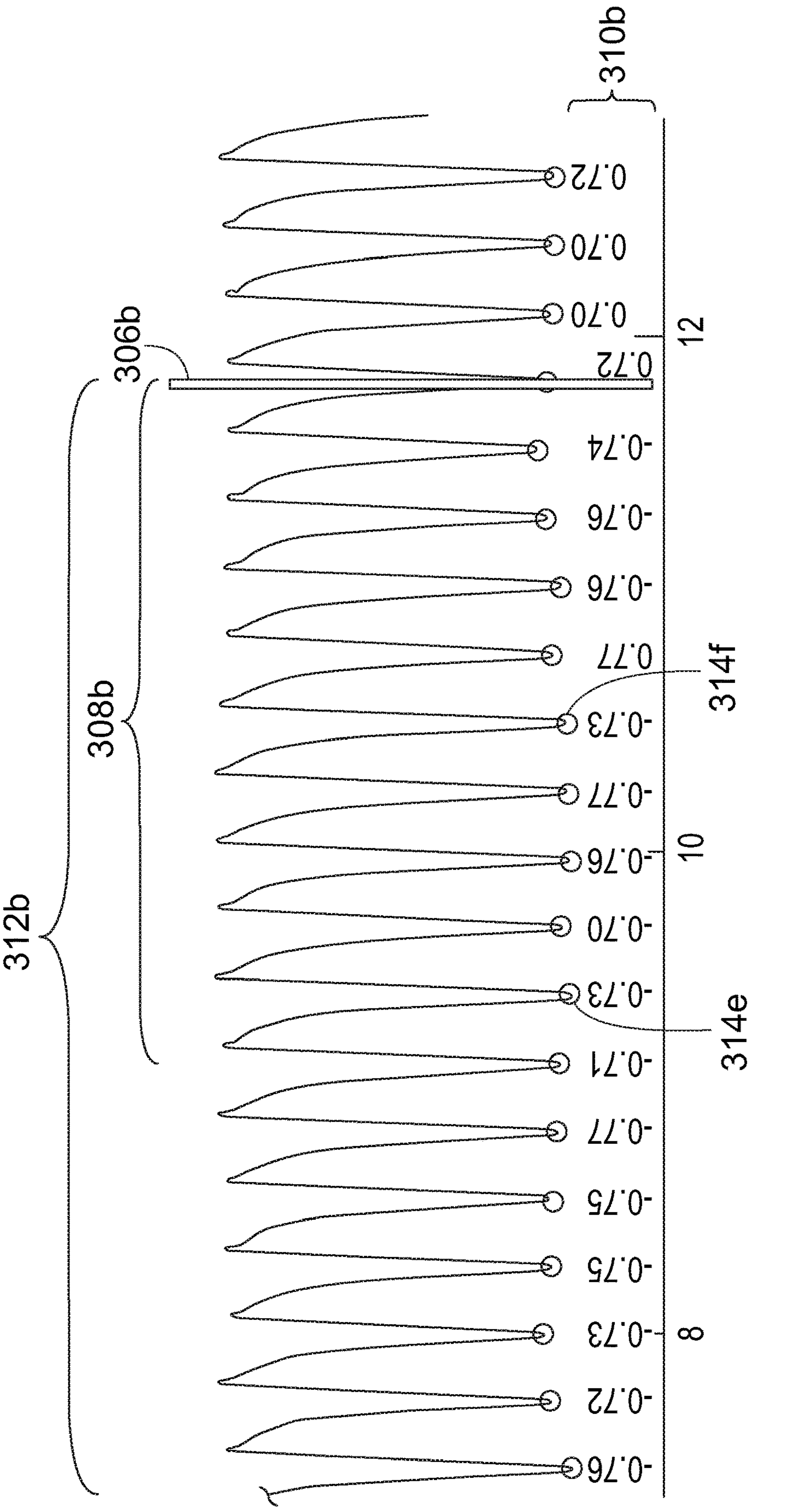
Figure 3C:
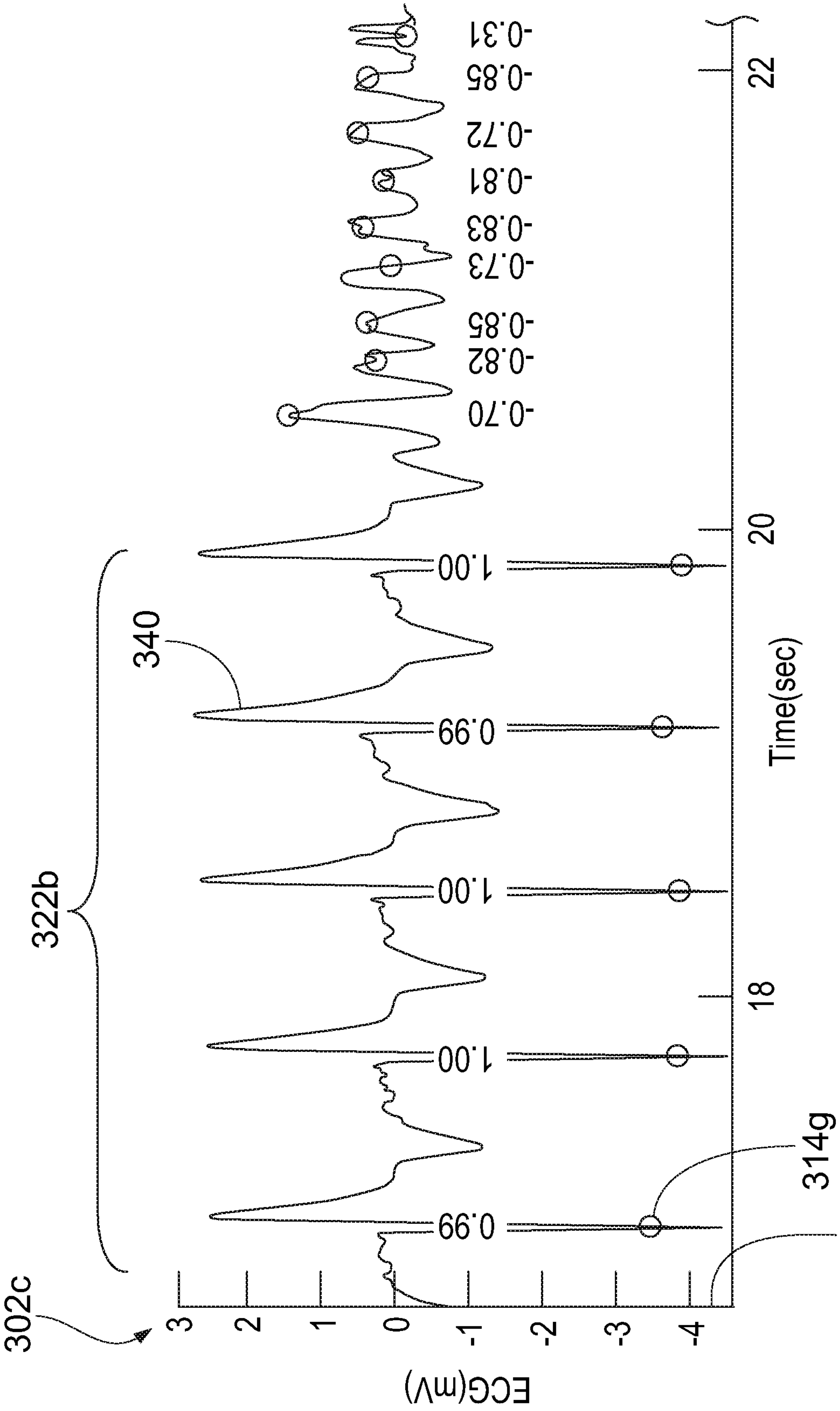
Figure 3C:
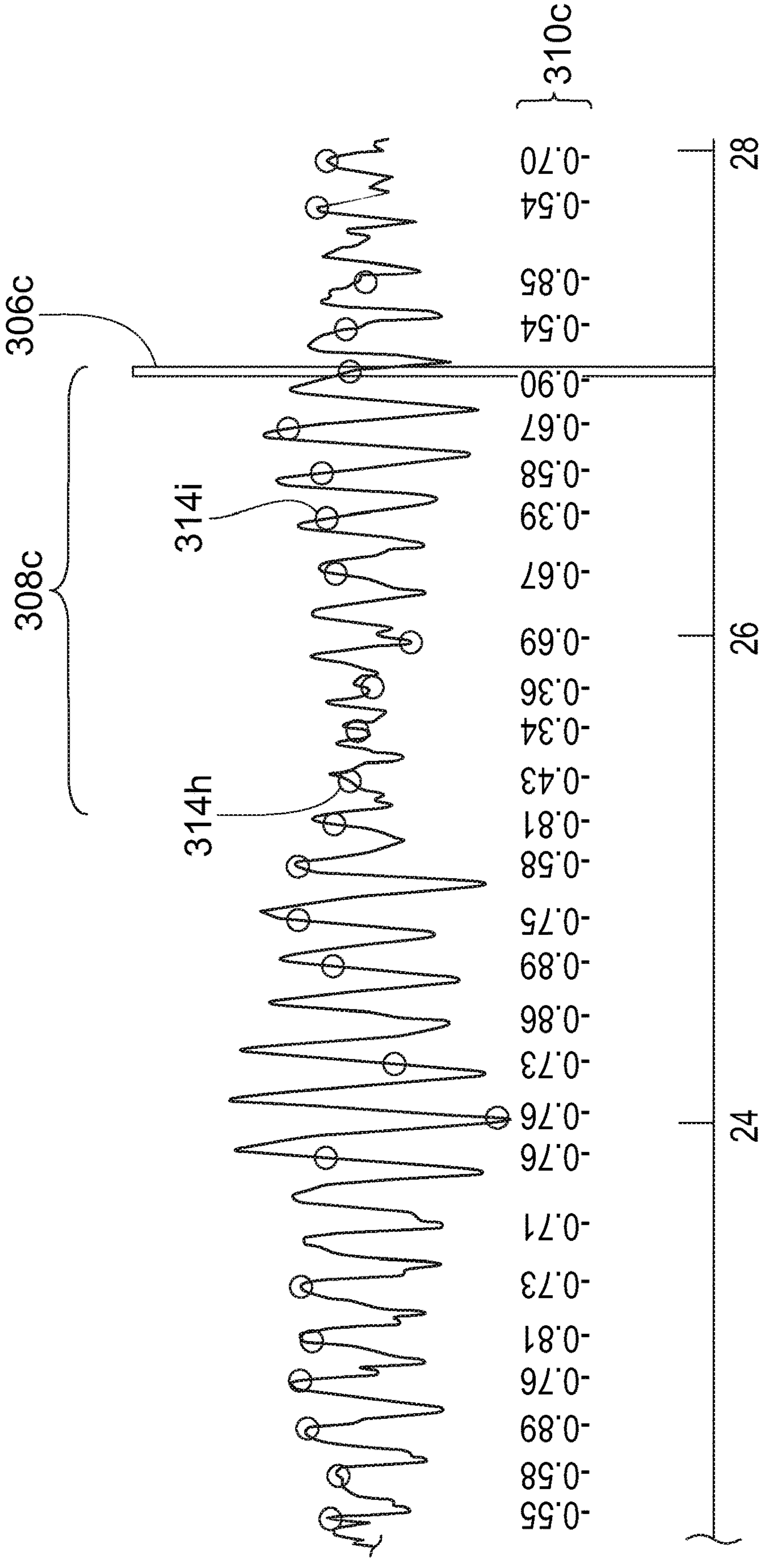

FIGS. 3A-3C illustrate example traces of SVT, MVT, and VF with correlation scores indicated for individual beats in accordance with embodiments herein. FIG. 3A illustrates an ECG episode characteristic during SVT atrial fibrillation in accordance with embodiments herein. Vertical axis 302*a* plots ECG trace 300 in millivolts while the horizontal axis 304*a* plots time in seconds. Line 306*a* indicates a point in time when a request is initiated to determine whether the trace 300 indicates SVT, MVT, or PVT/VF. For example, the request may be initiated in response to a heart rate level exceeding a threshold. The one or more processors can evaluate data for the previous X heart cycles, as indicated by most recent beats 308*a*. Correlation scores 310*a* are indicated corresponding with each heart cycle. The trace 300 indicates SVT as the correlation scores 310*a* evaluated within the most recent beats 308 are predominately high and stable (e.g., 0.99 to 1.0), wherein, for example, three out of ten beats have a similarity score greater than 90 percent. In some embodiments, the amount of time the device looks in the past may be limited to only the most current correlation scores, such as 10 scores. In other embodiments, the one or more processors can evaluate more data, such as for the beats within section 312*a* (e.g., more than 10 scores, 20 scores, 30 scores). Accordingly, the number of beats (e.g., X out of Y) that are evaluated is not limited to 10 and can, in some cases, be set by the practitioner and may not be the same for each patient. Furthermore, in some embodiments the most recent beats 308 can exclude one or more beats closest to the request line 306.

FIG. 3B illustrates an ECG episode characteristic during transition from sinus rhythm to MVT in accordance with embodiments herein. Again, vertical axis 302*b* plots ECG trace 320 in millivolts while the horizontal axis 304*b* plots time in seconds. Line 306*b* indicates a point in time when a request is initiated to determine whether the trace 320 indicates SVT, MVT, or PVT/VF. The one or more processors can evaluate data for the previous X heart cycles, as indicated by most recent beats 308*b*. Correlation scores 310*b* are indicated corresponding with each heart cycle, and the trace 320 indicates MVT as the correlation scores 310*b* of the most recent beats 308*b* are poor and stable (e.g., −0.77 to −0.70). Further, the trace 320 has stable R-wave peak amplitudes within the more recent beats 308*b* (and section 312*b*) and larger in amplitude compared to sinus QRS-wave peak amplitude, indicated in section 322*a*, as well as a stable heart rate.

FIG. 3C illustrates an ECG episode characteristic during transition from sinus rhythm to VF in accordance with embodiments herein. The vertical axis 302*c* plots ECG trace 340 in millivolts while the horizontal axis 304*c* plots time in seconds. Line 306*c* indicates the point in time when a request is initiated to determine whether the trace 340 indicates SVT, MVT, or PVT/VF. The one or more processors evaluate data for the previous X heart cycles (e.g., most recent beats 308*c*). Correlation scores 310*c* are associated with each detected beat and indicate VF having poor unstable correlation scores (e.g., −0.34 to −0.90). The trace 340 has smaller unstable R-wave peak amplitudes within the most recent beats 308*c* compared to sinus QRS, indicated in section 322*b*, as well as a very fast unstable heart rate.

Returning to FIG. 2A, at 212, the one or more processors determine whether MVT correlation scores conditions are met. In some embodiments, the one or more processors determine that i) the correlation scores are indicative of non-SVT morphology by comparing the correlation scores of a number of beats (e.g., most recent beats 308) to a correlation threshold, and ii) that the correlation scores are stable by determining correlation variability scores for the number of beats. For example, if X out of Y correlation scores are less or smaller than a correlation threshold (e.g., 7 out of 10 scores<0.9 (or about 0.85)), the correlation scores indicate that the rhythm has non-SVT morphology (e.g., MVT or PVT/VF). With respect to stability, if X out of Y correlation scores are stable (e.g., at least 6 out of 10 scores have absolute difference to mean or median e.g., correlation variability scores)<0.2 correlation points of the mean or median (e.g., correlation variability threshold), the rhythm is stable. For example, the correlation variability threshold can be i) an absolute value or ii) a percentage of the mean or median of correlation scores. A stable rhythm indicates that the morphology is repeating beat-to-beat without significant deviations.

If the correlation scores indicate that the rhythm has non-SVT morphology and that the rhythm is not stable, the process passes to 220 and the one or more processors diagnose the rhythm as PVT/VF, declaring a shockable diagnosis. In some cases, the one or more processors initiate treatment of the PVT/VF (e.g., shock therapy delivery), while in other cases, further analysis can be accomplished prior to treatment. Alternatively, if the correlation scores indicative of non-SVT morphology do not meet the criteria or correlation threshold, the process can return to 208 to further evaluate beats.

In some embodiments, the one or more processors can declare an MVT diagnosis when the conditions of 212 are met. If the correlation scores indicate that the rhythm has non-SVT morphology and is stable, the process passes to 222. In some embodiments, the one or more processors can accomplish further operations associated with block 222 as further discussed below.

In some cases, the one or more processors utilize the additional constraints of amplitude stability (214), heart rate stability (216) and/or QRS duration stability (218). At 214, the one or more processors determine whether MVT amplitude stability conditions are met. The amplitude stability condition can be evaluated based on i) absolute mean of the last Y QRS-wave peak amplitude (or R-wave peaks amplitude) is higher than safety ratio*sinus template QRS-wave peak amplitude (or R-wave peak amplitude) (e.g., to guard against misclassifying small amplitude VF as MVT), having, for example, a scaling factor=0.75 mV/mV (e.g., factor can be less than 1, etc.), and/or ii) amplitude of X out of Y QRS-wave peaks (or R-wave peaks) are stable (e.g., at least 7 out of 10 peaks have relative absolute deviation from mean (e.g., peak amplitude stability score)<a predetermined amplitude, such as about 0.1 mV).

Referring to FIGS. 3A-3C, circles 314 can indicate detected peak amplitudes; however the detected peak may change depending upon the rhythm or the traces. Although the detected peak amplitudes are discussed as R-wave peak amplitudes, it should be understood that QRS-wave peak amplitude is equally applicable. In FIG. 3A, circles 314*a*, 314*b*, 314*c* indicate peak amplitudes that are stable and approximately the same as the sinus QRS template amplitude (not shown). In FIG. 3B, circle 314*d* indicates the R-wave peak amplitude of the sinus QRS rhythm in section 322*a*, which is representative of the saved sinus QRS template. Circles 314*e*, 314*f* indicate a greater peak amplitude compared to the amplitude indicated by circle 314*d* and are stable beat to beat (e.g., repetitive, having similar amplitudes, etc.) as is experienced in MVT. FIG. 3C shows circle 314*g* in section 322*b* that is representative of the sinus QRS template amplitude (not shown). Circles 314*h*, 314*i* indicate amplitudes that are smaller than the sinus QRS template (e.g., amplitude indicated by the circle 314*g*). As can be seen within the section of most recent beats 308*c*, the amplitudes, not all are indicated separated, have high amplitude variability.

Returning to 214 in FIG. 2A, if the MVT amplitude stability conditions are not met, the process passes to 220 to declare the PVT/VF diagnosis (e.g., shockable diagnosis). If the MVT amplitude stability conditions are met, the process can, in some embodiments, pass to declare the MVT diagnosis at 222 or, in other embodiments, pass to 216 for further analysis of the most recent beats 308.

At 216, the one or more processors determine whether MVT heart rate stability conditions are met. The heart rate stability can be evaluated by determining whether a predetermined number of beats (e.g., the most recent beats 308) have RR intervals that are similar to each other. For example, the one or more processors can determine RR intervals associated with the number of beats, and determine a mean or median associated with the RR intervals. The one or more processors can compare a relative absolute difference of the RR intervals to the mean or median associated with the RR intervals. In some embodiments, the one or more processors can determine that the MVT heart rate is stable if at least 7 out of 10 RR intervals have relative absolute difference to the mean or median<a heart rate stability threshold, such as 20 msec (or about 20 msec).

If the MVT heart rate stability conditions are not met, the process passes to 220 to declare the PVT/VF diagnosis (e.g., shockable diagnosis). If the MVT heart rate stability conditions are met, the process can, in some embodiments, pass to declare the MVT diagnosis at 222 or, in other embodiments, pass to 218 for further analysis of the most recent beats 308.

At 218, the one or more processors determine whether MVT QRS duration stability conditions are met. For example, the one or more processors determine if the most recent beats 308 have sense-to-peak durations indicative of wide QRS complex and if the sense-to-peak durations within the most recent beats 308 are stable enough to guard against misclassifying irregular QRS duration VF as MVT. The one or more processors can determine durations of QRS complexes associated with the most recent beats 308, and determine a mean associated with the durations of the QRS complexes. The one or more processors can determine that a subset of the most recent beats 308 have durations of the QRS complexes that are equal to a duration of a QRS complex associated with the template or greater than a first predetermined time duration. The one or more processors can determine that a subset of beats within the most recent beats 308 have an absolute deviation from the mean associated with the durations of the QRS complexes that is less than a second predetermined time duration. In some embodiments, such as with respect to the wide QRS complex, the one or more processors can determine if sense-to-peak duration of at least 5 out of last 10 measurements (e.g., the most recent beats 308)>QRS width (e.g., duration) factor of 1*sinus template sense-to-peak duration or >90 msec (or about 90 msec). Further, with respect to stability, in some embodiments the one or more processors can determine if at least 6 out of 10 sense-to-peak durations (e.g., within the most recent beats 308) have absolute deviation from mean<30 msec (or about 30 msec).

If the MVT QRS duration stability conditions are not met, the process passes to 220 to declare the PVT/VT diagnosis (e.g., shockable diagnosis). If the MVT QRS duration stability conditions are met, the process passes to declare the MVT diagnosis at 222.

At 222, the one or more processors can declare an MVT diagnosis, postpone shock delivery, declare shock delivery postponement, and/or inhibit shock therapy delivery. For example, shock therapy delivery can be delayed to provide an opportunity for the MVT to self-terminate. In some embodiments, the process described in 212-218 can be accomplished multiple times (e.g., delay by 5 seconds up to three times) before a shocking intervention is initiated. For example, if the one or more processors declare an MVT diagnosis and inhibit shock therapy delivery, the one or more processors can wait five seconds before evaluating the next most recent beats 308. This process can repeat, such as a second and third time, to evaluate the MVT to see if the MVT subsequently qualifies as a PVT/VT or self-terminates. Further, less aggressive therapy may be implemented at 222. For example, user-programing of ATP therapy layers can be used. In some embodiments, the identification of MVT episodes allows the one or more processors to prioritize and/or re-try bursts of ATP therapy to resolve the arrythmia before defibrillation shock therapy, and/or deliver therapy based on rate alone, patient conditions, and/or clinician preference.

Although the process of FIG. 2A is described in connection with the use and comparison of one stored sinus QRS template, in some embodiments two, three, or more sinus QRS templates may be used, such as templates acquired at different rates. For example, each sinus QRS template can correspond to a different combination of electrodes that acquire FF signals. In some embodiments, a first template associated with FF sensing vector S4 (as shown in FIG. 1) between the RV coil electrode 136 and the CAN electrode can be stored in memory, and a second template associated with FF signals associated with FF sensing vector S5 between the RV tip electrode 132 and the CAN electrode can be stored in memory. The process of FIG. 2A therefore could, in some embodiments, compare the sensed FF cardiac signals (S4, S5) at 208 to both of the sinus templates (208) to determine morphology scores associated with each of the combinations of electrodes. The processing of 212-218 can be accomplished simultaneously for multiple channels of FF signals.

Figure 2B:
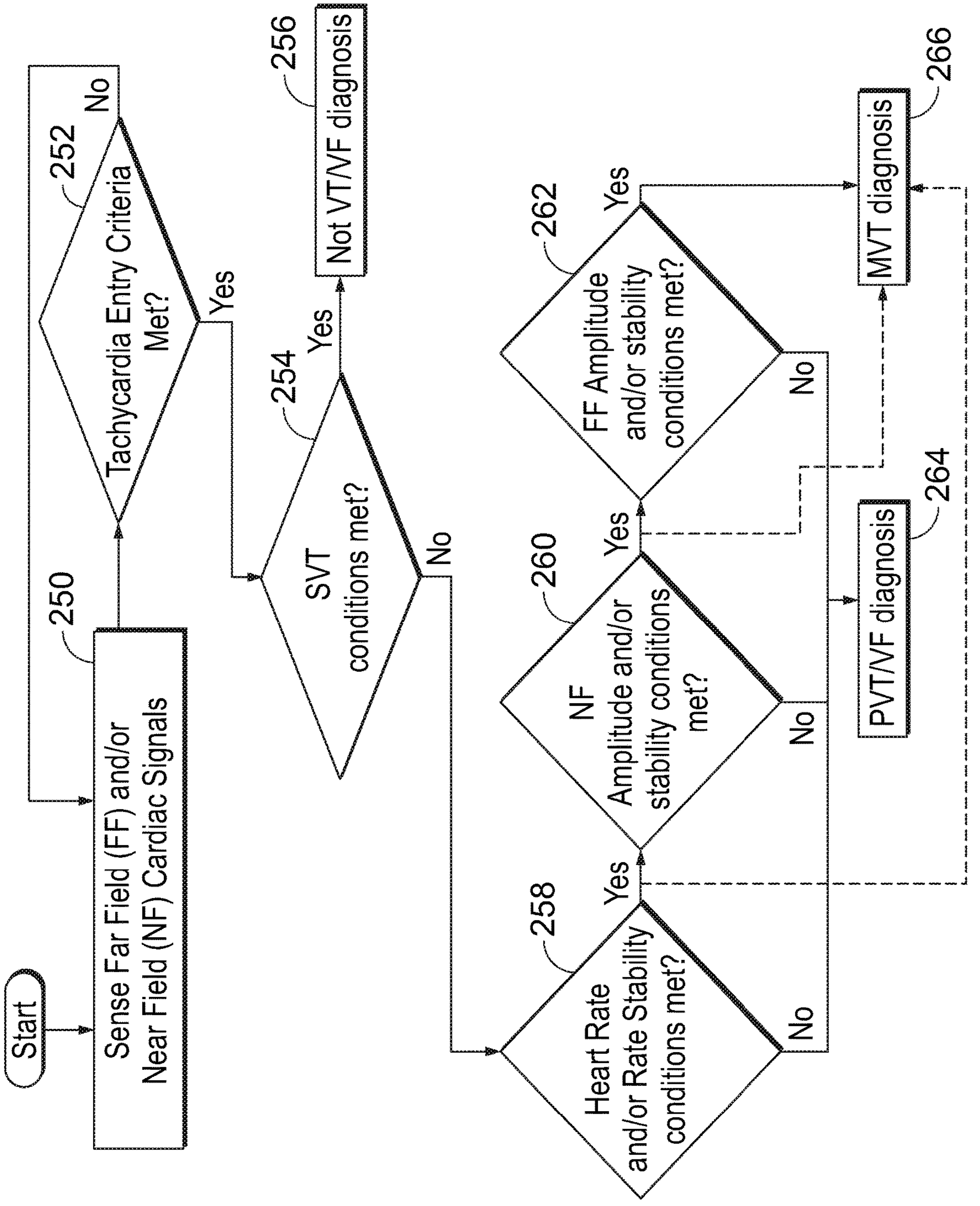
FIG. 2B illustrates another process for utilizing NF and FF signals to discriminate between SVT, MVT, and PVT/VF in accordance with embodiments herein.

FIG. 2B illustrates another process for utilizing NF and FF signals to discriminate between SVT, MVT and PVT/VF in accordance with embodiments herein. The operations of FIG. 2B may be implemented by hardware, firmware, circuitry and/or one or more processors housed partially and/or entirely within the IMD 100, a local external device, remote server or more generally within a healthcare system. Optionally, the operations of FIG. 2B may be partially implemented by an IMD 100 and partially implemented by a local external device, remote server or more generally within a healthcare system. For example, the IMD 100 includes IMD memory and one or more IMD processors, while each of the external devices/systems (e.g., local, remote, or anywhere within the healthcare system) include external device memory and one or more external device processors. In some embodiments, the discriminator methods described herein can all or partly be performed by firmware, software, hardware, etc., on a beat-by-beat basis or on-demand using buffered data. Further, the IMD 100 can be a subcutaneous IMD/ICD, a transvenous IMD/ICD, or other implantable cardiac monitor known in the art.

Under control of one or more processors within an IMD 100, at 250, sensors sense FF signals and/or NF signals between first and second combinations of electrodes coupled to the IMD 100 and/or to an external device. By way of example, an IMD 100 may sense FF and/or NF signals and internally and automatically implement the operations of FIG. 2B, discriminating between arrhythmias and oversensing conditions, and based thereon, postpone shock delivery, declare shock delivery postponement, declare an MVT diagnosis, inhibit shock therapy delivery, deliver the appropriate therapy (e.g., anti-tachycardia pacing, shock therapy delivery), and/or adjust sensing and/or therapy parameters. Additionally, or alternatively, the IMD 100 may sense the FF and/or NF signals, wirelessly convey the FF and/or NF signals in real time to an external device, where the external device performs all or a portion of the operations of FIG. 2B discussed herein. The external device discriminates between arrhythmias and oversensing conditions, and based thereon, the external device directs the IMD 100 to postpone shock delivery, declare shock delivery postponement, declare an MVT diagnosis, inhibit shock therapy delivery, deliver the appropriate therapy (e.g., anti-tachycardia pacing, shock therapy delivery, etc.), and/or adjust sensing and/or therapy parameters.

In accordance with embodiments herein, FF and/or NF signals may be sensed over a desired number of cardiac events/beats and/or may be continuously sensed for analysis. At 252, one or more processors determine whether tachycardia entry criteria are met. For example, tachycardia entry criteria can be met after a certain number of beats are sensed above a tachycardia rate therapy zone. In some embodiments, tachycardia entry criteria can be determined based on the parameters discussed with respect to block 204 of FIG. 2A. If the tachycardia entry criteria are not met, the process returns to 250. If the tachycardia entry criteria are met, the process passes to 254.

At 254, the one or more processors can implement a supraventricular (SVT) discrimination algorithm to determine whether the rhythm (e.g., sinus rhythm) is SVT in origin. In some embodiments, the one or more processors can utilize the FFM and other algorithms discussed in block 206 of FIG. 2A. In other embodiments, the one or more processors can utilize one or more of sudden onset [SO], interval stability [IS], bigeminy qualifier [BQ], AV association [or AVA or rate branch], among others. If the rhythm is determined to be SVT in origin and thus not a shockable event, the process passes to 256. Other treatment and/or analysis may be accomplished concerning the SVT rhythm.

If the SVT conditions are not met at 254, the process determines, based on one or more conditions (e.g., condition sets wherein each set can include one or more conditions), whether to declare an MVT diagnosis or a PVT/VF diagnosis. For example, heart rate and/or rate stability conditions at 258, NF amplitude and/or stability conditions at 260 and FF amplitude and/or stability conditions at 262 can be evaluated consecutively, in any order, and/or simultaneously. Further, the MVT diagnosis (266) can be declared after one, two, three, or all four of the conditions are met. Therefore, it should be understood that after any one or more of the condition sets are not met, the process can declare a shockable diagnosis (e.g., PVT/VF diagnosis) (264), and in some cases, the one or more processors can initiate shock therapy delivery or other processing and/or sensing algorithms as are known in the art. For example, episodes of MVT and PVT/VF can be handled by user-programing of ATP therapy layers followed by defibrillation shock layers within therapy zones (VT1, VT2, VF). In some embodiments, the identification of MVT episodes allows the one or more processors to prioritize and/or re-try bursts of ATP therapy to resolve the arrythmia before defibrillation shock therapy.

Returning to FIG. 2B, at 258, the one or more processors determine whether heart rate and/or rate stability conditions are met. Although four conditions are indicated, the one or more processors can determine that the conditions are met based on one, two, three, or all four of the conditions being met. In some embodiments, the one or more processors determine that i) in the most recent number (Y) (e.g., most recent beats 308) of beat-to-beat RR intervals, the mean RR interval is greater than a heart rate threshold (Z) (e.g., Y=10 beats and Z=400 msec); ii) In the most recent number (Y) of beat-to-beat RR intervals, the range (e.g., maximum RR−minimum RR) of RR intervals excluding highest and lowest outliers is less than a heart rate range stability threshold (Z) (e.g., Y=8 beats and Z=40 msec); iii) in the most recent number (Y) RR intervals, the largest absolute beat-to-beat interval difference is less than a heart rate stability threshold (Z) (e.g., Y=10 beats and Z=40 msec); and/or iv) in the most recent number (Y) of RR intervals, the percentage of RR intervals with absolute difference less than a heart stability threshold (Z) is above a certain percentage (P) (e.g., predetermined percentage) (e.g., Y=10, P=80%, Z=40 msec).

If the heart rate and/or rate stability conditions are not met, the process passes to 264 and the one or more processors diagnose the rhythm as PVT/VF, declaring a shockable diagnosis. In some cases, the one or more processors initiate treatment of the PVT/VF (e.g., shock therapy delivery), while in other cases, further analysis can be accomplished prior to treatment. Alternatively, if the heart rate and/or rate stability conditions are met, the process passes to 260 or 266.

Referring to blocks 260 and 262, the same set of conditions can be applied. However, the threshold "Z" can be different for the NF and FF signals, as the NF signal has a higher amplitude than the FF signal.

At 260, the one or more processors determine whether NF amplitude and/or stability conditions are met. Again, although four conditions are indicated, the one or more processors can determine that the conditions are met based on one, two, three, or all four of the conditions being met. In some embodiments, the one or more processors determine that i) in the most recent number (Y) of QRS-wave peaks, a mean of absolute peak amplitudes is higher than a specific voltage threshold (Z) (e.g., Y=10, Z=6 mV); ii) in the most recent number (Y) of QRS-wave peaks, at least a certain number (X) have absolute peak amplitude higher than a specific voltage threshold (Z) (e.g., Y=10, X=8, Z=6 mV); iii) in the most recent number (Y) of QRS-wave peaks, a mean of absolute difference of beat-to-beat peak amplitudes is lower than a specific voltage threshold (Z) (e.g., Y=10, Z=2 mV); and/or iv) in the most recent number (Y) of QRS-wave peaks, at least a certain number (X) have an absolute difference of beat-to-beat peak amplitudes below an amplitude stability threshold (Z) (e.g., Y=10, X=8, Z=0.2 mV). It should be understood that the values of X, Y, and Z are exemplary and not limiting, and that other values and ranges of values are contemplated.

If the NF amplitude and/or stability conditions are not met, the process passes to 264 and the one or more processors diagnose the rhythm as PVT/VF, declaring a shockable diagnosis. Alternatively, if the NF amplitude and/or stability conditions are met, the process passes to 262 or 266.

At 262, the one or more processors determine whether FF amplitude and/or stability conditions are met. Again, although four conditions are indicated, the one or more processors can determine that the conditions are met based on one, two, three, or all four of the conditions being met. In some embodiments, the one or more processors determine that i) in the most recent number (Y) of QRS-wave peaks, the mean of absolute peak amplitudes is higher than specific voltage threshold (Z) (e.g., Y=10, Z=1.5 mV); ii) in the most recent number (Y) of QRS-wave peaks, at least a certain number (X) have absolute peak amplitude higher than specific voltage threshold (Z) (e.g., Y=10, X=8, Z=1.5 mV); iii) in the most recent number (Y) of QRS-wave peaks, the mean of absolute difference of beat-to-beat peak amplitudes is lower than specific voltage threshold (Z) (e.g., Y=10, Z=0.15 mV); and/or iv) in the most recent number (Y) of QRS-wave peaks, at least a certain number (X) have an absolute difference of beat-to-beat peak amplitudes below an amplitude stability threshold (Z) (e.g., Y=10, X=8 , Z=0.15 mV). It should be understood that the values of X, Y, and Z are exemplary and not limiting, and that other values and ranges of values are contemplated.

If the FF amplitude and/or stability conditions are not met, the process passes to 264 and the one or more processors diagnose the rhythm as PVT/VF, declaring a shockable diagnosis. Alternatively, if the FF amplitude and/or stability conditions are met, the process passes to 266.

At 266, the one or more processors can declare an MVT diagnosis, postpone shock delivery, declare shock delivery postponement, and/or inhibit shock therapy delivery. For example, shock therapy delivery can be delayed, providing an opportunity for the MVT to self-terminate, ATP therapy can be provided, etc. In some embodiments, the process described in 258-262 can be accomplished multiple times (e.g., delay by 5 seconds up to three times, etc.) before a shocking intervention is initiated. For example, if the one or more processors declare an MVT diagnosis and inhibit shock therapy delivery, the one or more processors can wait five seconds before evaluating the next most recent beats 308. This process can repeat, such as a second and third time, to evaluate the MVT to see if the MVT subsequently qualifies as a PVT/VT or self-terminates.

Further, the processing of 258-262 can be accomplished simultaneously for multiple channels of NF signals and/or multiple channels of FF signals.

In addition, different combinations of the conditions discussed in blocks 258, 260, and 262 can be combined to either declare PVT/VF diagnosis 264 or declare MVT diagnosis 266. For example, if the heart rate stability condition is not met (e.g., using a threshold X1) at 258, the one or more processors declare a PVT/VT diagnosis at 264. In another example, if the heart rate stability condition is met (e.g., using a threshold B1) and the heart rate condition is met (e.g., using a threshold B2) at 258, the one or more processors declare an MVT diagnosis 266. In yet another example, if the heart rate stability condition is met (e.g., using a threshold A1) at 258 and the NF amplitude stability condition is met (e.g., using a threshold A2) at 260, the one or more processors declare an MVT diagnosis 266. In a further example, if the heart rate condition is met (e.g., using a threshold C1) at 258, and the NF amplitude condition is met (e.g., using a threshold C2), the one or more processors declare an MVT diagnosis 266. Not all of the possible combinations are specifically indicated, and it should be understood that other combinations of conditions discussed in blocks 258, 260, and 262 can be used.

The attributes discussed in FIG. 2A and FIG. 2B, namely correlation, amplitude, heart rate, and QRS duration, can also be used to determine oversensing or double sensing within the most recent beats 308. The process of FIG. 2A, and especially 212-218, can also be used to detect oversensing of R waves, P waves, and/or T waves. By detecting oversensing, the one or more processors can prevent a rhythm that is an MVT from being erroneously identified as a PVT, and thus inhibit unnecessary shock therapy and/or other therapies (e.g., anti-cardiography therapy).

Figure 4A:
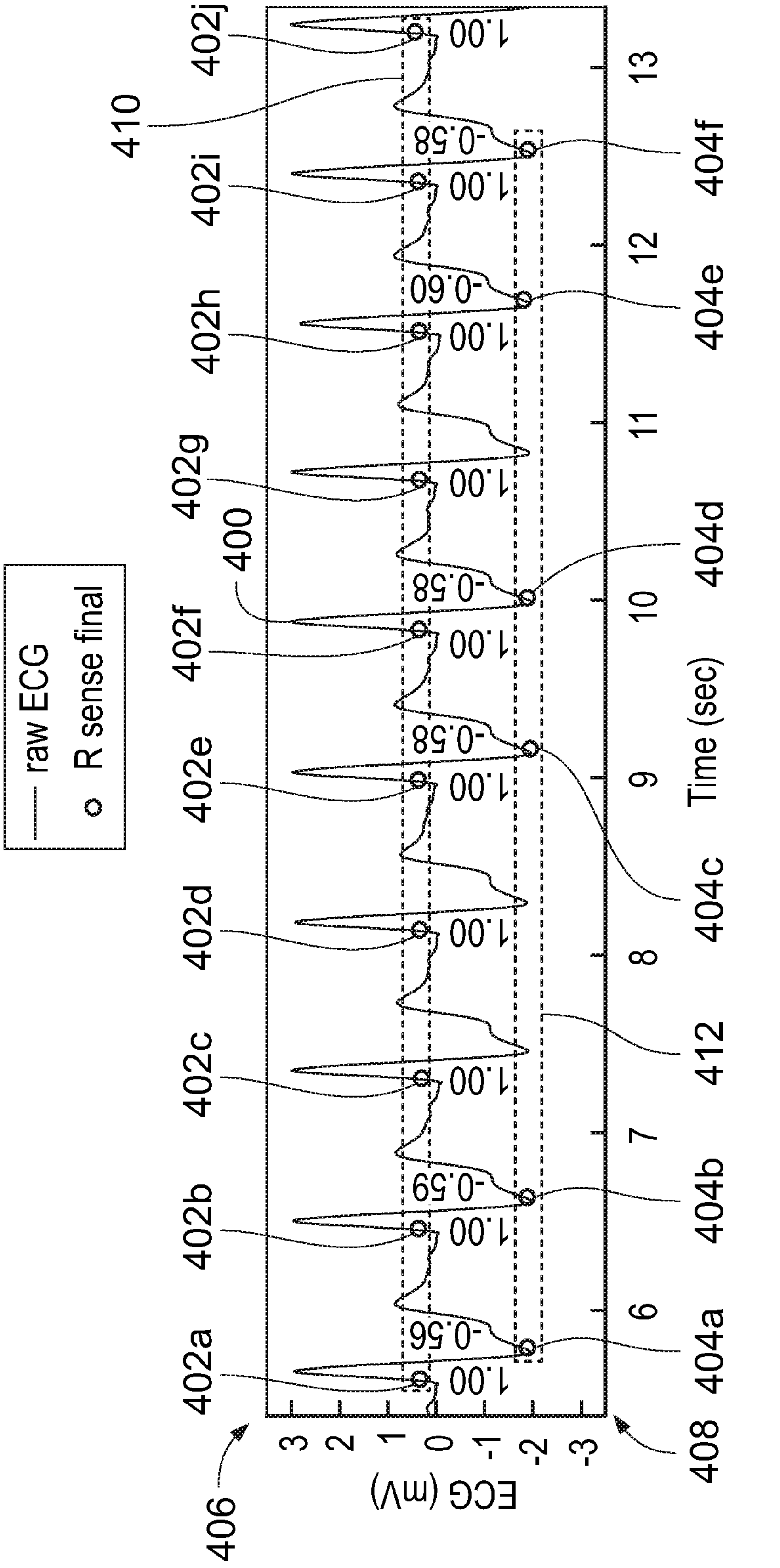
FIGS. 4A and 4B illustrate clustering patterns of ECG characteristics to identify double sensing or double counting scenarios that can be used to distinguish false tachycardia symptoms in accordance with embodiments herein.
Figure 4B:
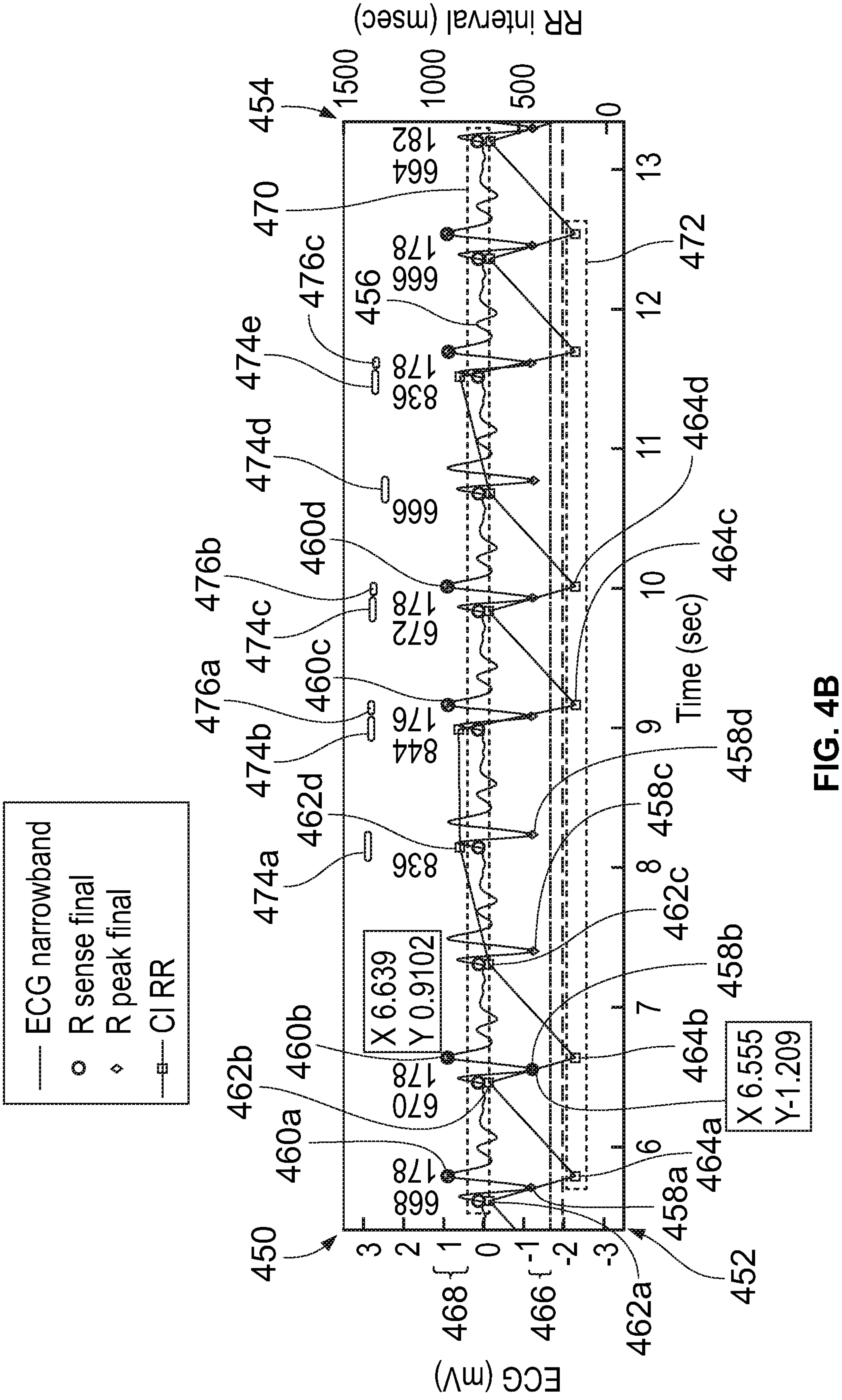

FIGS. 4A and 4B illustrate clustering patterns of ECG characteristics to identify double sensing or double counting scenarios that can be used to distinguish false tachycardia symptoms in accordance with embodiments herein. For example, the methodology of FIG. 2A (e.g., 212-218) can be applied to ECG traces to identify when the trace does not indicate either PVT, MVT, or SVT. In some embodiments the double sensing can occur on wide QRS, and in other embodiments, two clustering patterns for each characteristic can be identified, although the embodiments herein are not so limited.

In some embodiments, the two clusters-pattern can be identified based on the smallest Y/2 most recent values (e.g., mean and deviation from mean of the smallest 5 out of 10 peak R-wave amplitudes/correlation scores/heart rate/QRS duration) and the largest Y/2 values (e.g., mean and deviation from mean of the largest 5 out of 10 peak R-wave amplitudes/correlation scores/heart rate/QRS duration). In other embodiments, the mean of the top and bottom percentiles (e.g., top mean and bottom mean) along with the mean absolute deviation from top/bottom mean could be used to define two clusters and test whether the most recent Y values form a two-cluster pattern. For example, in some embodiments top mean=mean top 5 values, bottom mean=mean bottom 5 values. IF (mean top 5 values>0.9) AND (mean absolute deviation from top mean of top 5 values<0.2) AND (mean absolute deviation from bottom mean of bottom 5 values<0.2), THEN 2-cluster pattern of oversensing is identified. It should be understood that the values defined herein may be approximate, such that, for example, the top mean of top 5 values<about 0.2, the mean absolute deviation from bottom mean of bottom 5 values<about 0.2, and so on.

In some embodiments, the two clusters-pattern may be identified through comparison of the peak amplitudes of consecutive R-waves without calculation of a mean or median peak R-wave amplitude. The comparison of peak amplitudes of consecutive R-waves may be used to determine whether the peak R wave amplitude for the first R wave in a pair of consecutive R waves is larger, smaller, or equal to the peak R wave amplitude for the second R wave in that same pair, and vice versa. If the peak amplitude is consistently larger for the first R wave in every other pair of two R waves detected as part of a heart rhythm and the peak amplitude is consistently smaller for the second R wave in every other pair when compared to the first R wave of the next pair, or vice versa, an oversensing pattern is indicated. In this case, tachycardia therapy delivery may be inhibited or the heart rhythm may be re-assessed after consideration of the suspected oversensed R waves.

The following example describes identifying the two clusters-pattern through comparison of the peak amplitudes of consecutive R-waves (e.g., without calculation of a mean or median peak R-wave amplitude). A sinus rhythm with R-wave amplitude of 1.0 mV and T-wave amplitude of 0.5 mV is considered. The IMD 100 oversenses every T-wave and records the peak amplitudes for a series of consecutive sensed beats (e.g., 10 consecutive sensed beats) as the IMD 100 assesses SVT/MVT/PVT/Oversensing. For ease of comparison, odd numbered beats (e.g., beats 1, 3, 5, 7, 9) have peak amplitudes of 1.0 mV and even numbered beats (e.g., beats 2, 4, 6, 8, 10) have peak amplitudes of 0.5 mV.

One or more processors compare beats 1 and 2 and determine that beat 2 has a lower peak amplitude (e.g., 0.5 mV) than the beat 1 (e.g., 1.0 mV). A comparison of beats 2 and 3 determines that beat 3 (e.g., 1.0 mv) has a higher peak amplitude than the previous beat 2 (e.g., 0.5 mv). A comparison of beats 3 and 4 determines that beat 4 (e.g., 0.5 mV) has a lower peak amplitude than the previous beat 3 (e.g., 1.0 mV). A comparison of beats 4 and 5 determines that beat 5 (e.g., 1.0 mV) has a higher peak amplitude than the previous beat 4 (e.g., 0.5 mV). Therefore, the peak amplitude is consistently larger for the first R wave in every other pair of two R waves detected as part of a heart rhythm and the peak amplitude is consistently smaller for the second R wave in every other pair when compared to the first R wave of the next pair, or vice versa, and thus therapy delivery can be inhibited.

In further embodiments, also related to identifying the two clusters-pattern through comparison of the peak amplitudes of consecutive R-waves, a threshold can be used to avoid random fluctuations (e.g., during beathing) that may falsely trigger oversensing logic.

FIG. 4A shows correlation score clustering of R-waves that are correctly sensed and incorrect oversensed R-waves. Vertical axis 406 plots ECG trace 400 in millivolts while the horizontal axis 408 plots time in seconds. The ECG trace 400 (e.g., raw ECG) is shown with R-waves 402*a*-402*j* that have an associated correlation score of 1.00. The R-waves 402 are located on a positive deflection of the trace 400. Oversensed R-waves 404*a*-404*f* having correlation scores between −0.56 and −0.60 are also shown. For example, the R-wave 402*a* and the oversensed R-wave 404*a* are located on the same R-wave. The correlation scores of the R-waves 402 form a first cluster 410 and the correlation scores of the oversensed R-waves 404 form a second cluster 412, wherein each cluster 410, 412 includes the same and/or similar correlation scores.

FIG. 4B shows sensed peak amplitude, RR interval, and sense-to-peak duration clustering of oversensed R-waves. Left vertical axis 450 plots ECG trace 456 in millivolts, horizontal axis 452 plots time in seconds, and right vertical axis 454 plots RR interval in milliseconds. R-wave peak amplitudes 458*a*-458*d* (not all are separately indicated) cluster to about −1.21 mV (e.g., indicated with cluster 466). Oversensed R-wave amplitudes 460*a*-460*d* (not all are separately indicated) cluster to about 0.92 mV (e.g., indicated with cluster 468). RR intervals 462*a*-462*d* (not all are separately indicated) cluster to about 668 msec (e.g., indicated with cluster 470), while oversensed RR intervals 464*a*-464*d* (not all are separately indicated) cluster to about 178 msec (e.g., indicated with cluster 472). Sense-to-peak durations 474*a*-474*e* cluster to about 96 msec (indicated as extending between approximately R sense final and R peak final as indicated), and oversensed sense-to-peak durations 476*a*-476*c* cluster to about 4 msec (indicating double counted QRS-wave). The identification of the two distinct clusters associated with one or more of the correlation scores, sensed peak amplitude, RR interval, and sense-to-peak duration can be used to determine that a tachycardia event is not occurring and inhibit tachycardia therapy (e.g., shock therapy).

Figure 4C:
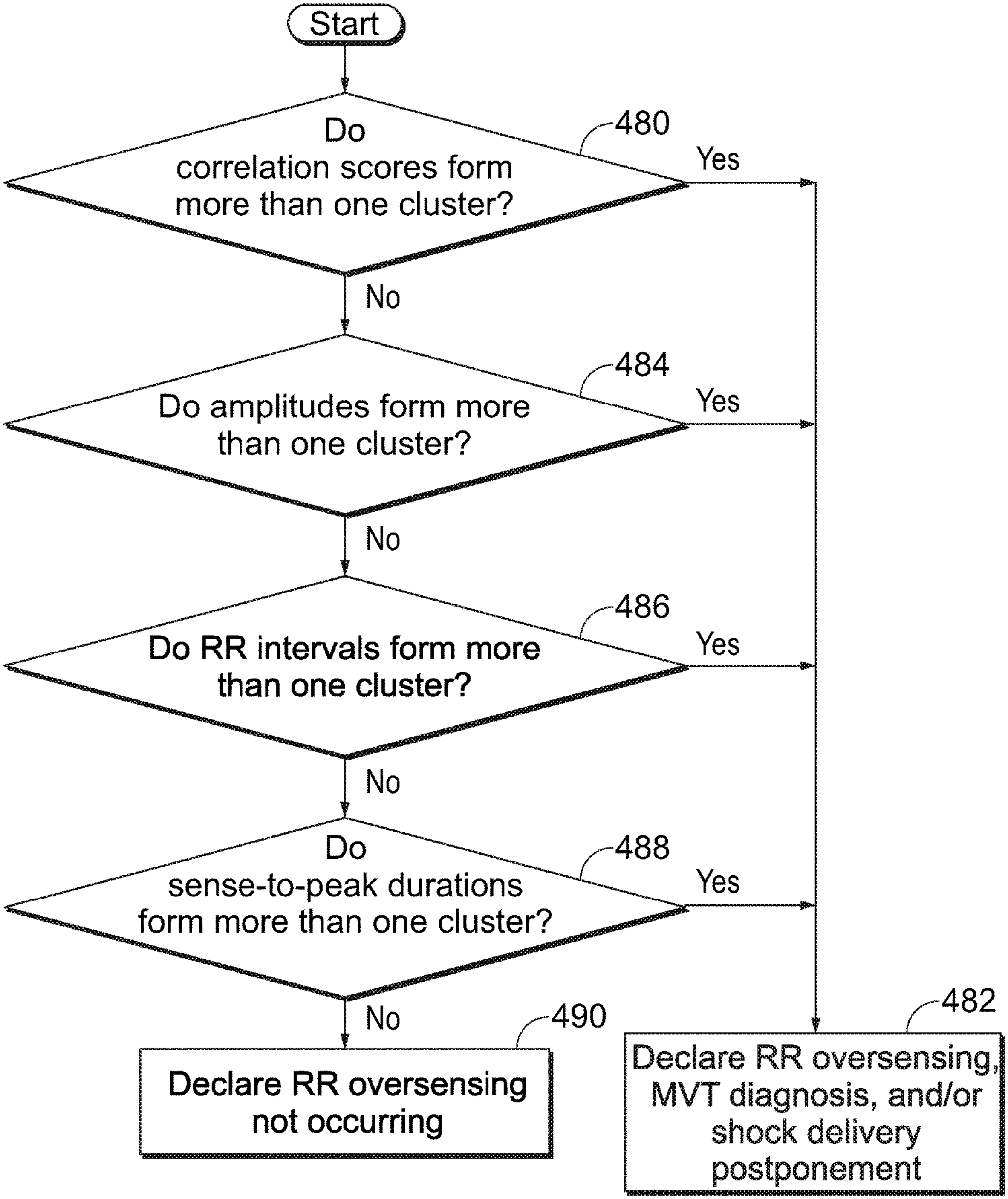
FIG. 4C illustrates a process for determining if oversensing of R-waves is occurring such that tachycardia therapy (e.g., anti-tachycardia pacing or defibrillation shock) should be postponed and/or inhibited in accordance with embodiments herein.

FIG. 4C illustrates a process for determining if oversensing of R-waves is occurring such that tachycardia therapy (e.g., anti-tachycardia pacing or defibrillation shock) should be postponed and/or inhibited in accordance with embodiments herein. The operations of FIG. 4C may be implemented by hardware, firmware, circuitry and/or one or more processors housed partially and/or entirely within an IMD, a local external device, remote server or more generally within a healthcare system. Optionally, the operations of FIG. 4C may be partially implemented by an IMD and partially implemented by a local external device, remote server or more generally within a healthcare system. For example, the IMD includes IMD memory and one or more IMD processors, while each of the external devices/systems (e.g., local, remote, or anywhere within the healthcare system) include external device memory and one or more external device processors. In some embodiments, the methods described herein can all or partly be performed by firmware, software, hardware, etc., on a beat-by-beat basis or on-demand using buffered data.

At 480, the one or more processors determine if correlation scores of the R-waves form more than one cluster. If more than one cluster 410, 412 is formed as discussed previously, RR oversensing can be occurring and the process passes to 482, where the one or more processors can declare RR oversensing, postpone shock delivery, declare shock delivery postponement, declare MVT diagnosis, inhibit tachycardia therapy and/or accomplish further processing and analysis. If one cluster is identified, the process passes to 484.

In other embodiments, the one or more processors can determine that RR oversensing can be occurring after additional conditions are met, such as one or more of 484, 486, and 488 discussed below. In some embodiments, one, two, or more of any combination of the conditions of 480, 484, 486, and 488 can be used to identify RR oversensing, postpone shock delivery, declare shock delivery postponement, and/or declare MVT diagnosis (482).

At 484 the one or more processors determine if amplitudes of the signal form more than one cluster. For example, R-wave peak amplitudes 458 and oversensed R-wave amplitudes 460 form separate and distinct clusters 466, 468 as discussed above. If more than one cluster is identified, the process can pass to 482. If one cluster is identified, the process passes to 486 where the one or more processors determine if RR intervals form more than one cluster. For example, the RR intervals 462 and the oversensed RR intervals 464*a*-464 form separate and distinct clusters 470, 472. If more than one cluster is identified, the process can pass to 482. If one cluster is identified, the process passes to 488 and the one or more processors determine if sense-to-peak durations 474 and oversensed sense-to-peak durations 476 form separate and distinct clusters. As shown in FIG. 4B, the sense-to-peak durations 474 and the oversensed sense-to-peak durations 476 form separate and distinct clusters based on different lengths of time. If more than one cluster is identified, the process passes to 482. If one cluster is identified, the process passes to 490 and the one or more processors determine that RR oversensing is not occurring.

Figure 5A:
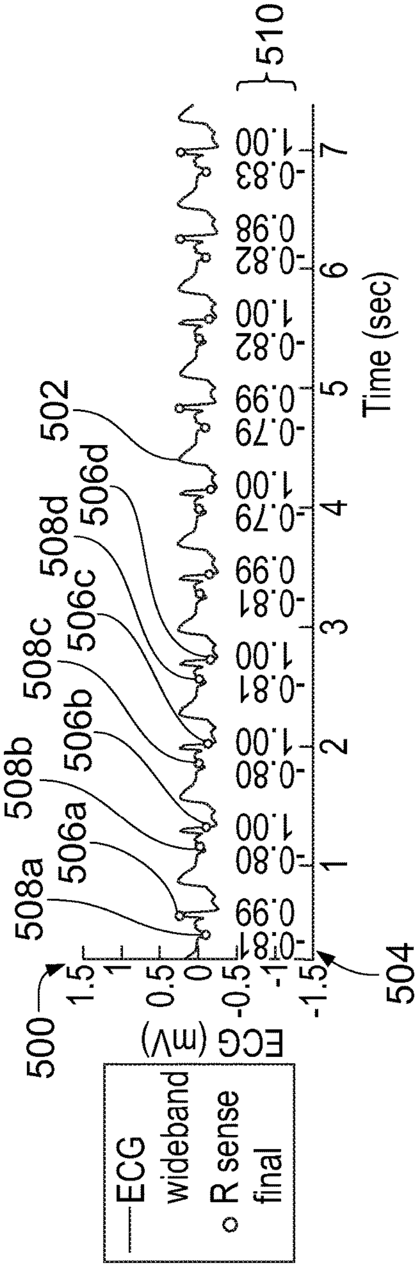
FIGS. 5A and 5B illustrate clustering patterns of ECG characteristics to identify oversensing scenarios, such as of P-wave and/or T-wave oversensing, that can be used to distinguish false tachycardia symptoms in accordance with embodiments herein.
Figure 5B:
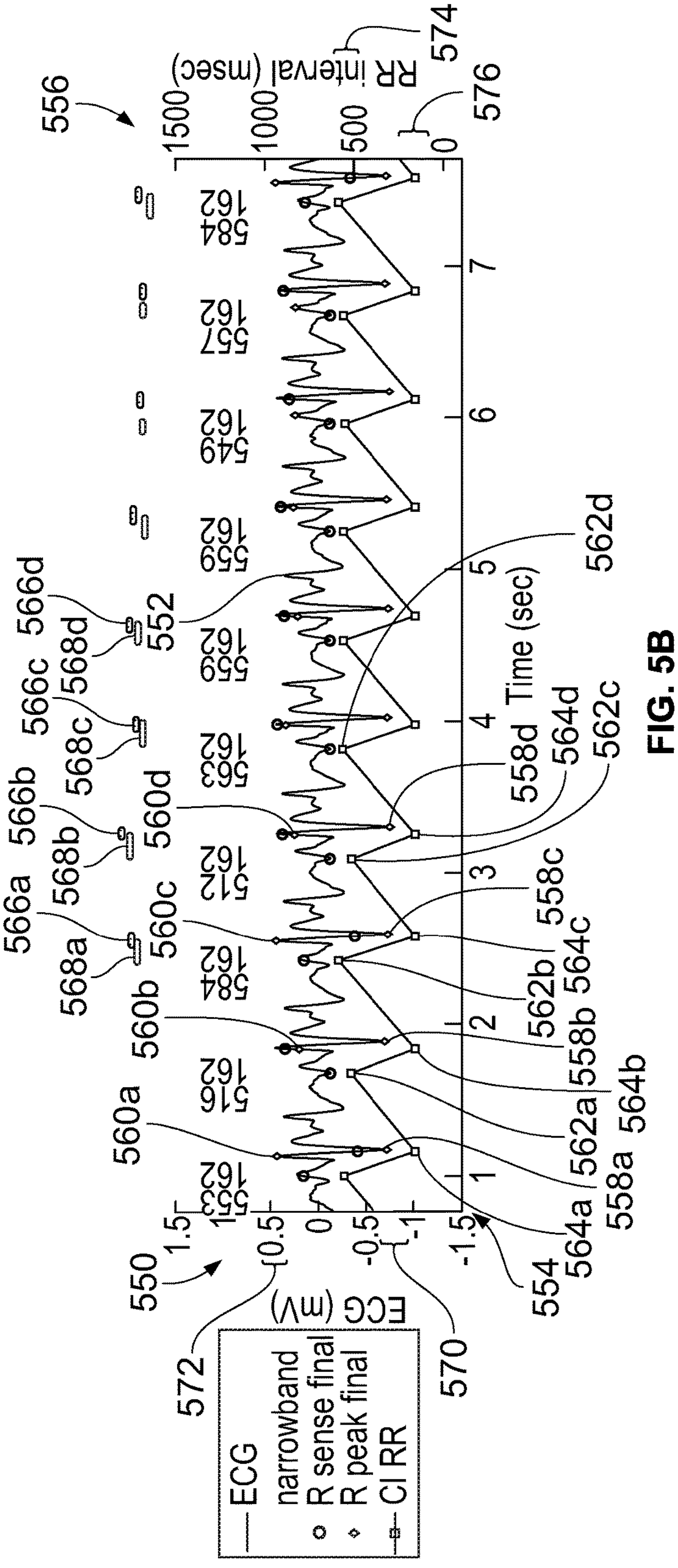

FIGS. 5A and 5B illustrate clustering patterns of ECG characteristics to identify oversensing scenarios, such as of P-wave and/or T-wave oversensing, that can be used to distinguish false tachycardia symptoms in accordance with embodiments herein. Again, the methodology of FIG. 2A (e.g., 212-218) can be applied to ECG traces to identify when the trace does not indicate PVT, MVT, or SVT. In some embodiments the oversensing can occur on wide QRS, and in other embodiments, two clustering patterns for each characteristic can be identified, although the embodiments herein are not so limited. Further, the two clusters-pattern can be determined/identified as discussed previously with respect to FIGS. 4A and 4B. For example, the two clusters-pattern can be determined for amplitudes, heart rate and sense-to-peak duration. The variation thresholds can be +/−0.2 for correlation, +/−0.1 mV for QRS-wave peak, +/−50 msec for RR interval and +/−10 msec for sense-to-peak duration.

FIG. 5A illustrates oversensing of P-waves on an ECG trace and correlation score clustering associated with R-waves that are correctly sensed and P-waves that are incorrectly sensed as R-waves. As discussed above, the correlations scores are a result of morphology matching by comparing the instant waveform with the saved template. In some cases, a P-wave may be erroneously detected as an R-wave if it crosses a threshold. As shown, both P-waves and R-waves are indicated with a circle as "R sense final", which would indicate to the one or more processors an erroneous much faster heart rate (VT/VR). Although the example of P-waves is discussed in detail herein, it should be understood that the methodology applies equally to T-waves (not shown).

Left vertical axis 500 plots ECG trace 502 in millivolts and horizontal axis 504 plots time in seconds. The trace 502 can be, for example, an ECG wideband signal. R-waves

506*a*-506*d* (not all are separately indicated) are indicated on the trace 502 and each has an associated correlation score 510. For example, the R-wave 506*a* has a correlation score of 0.99, the R-wave 506*b* has a correlation score of 1.00, and so on, for a correlation score cluster value of around 1.00. P-waves 508*a*-508*d* (not all are separately indicated) are also indicated on the trace 502 and each has an associated correlation score 510. The P-wave 508*a* has a correlation score of −0.81, the P-wave 508*b* has a correlation score of −0.80, and so on, for a correlation score cluster value of around −0.81. The correlation scores of the R-waves 506 form a first cluster (e.g., around the correlation score of approximately 1.00) and the correlation scores of the oversensed P-waves 508 form a second cluster (e.g., around the correlation score of approximately −0.81), wherein each distinct cluster includes the same and/or similar correlation scores. The two distinct clusters can be used to determine that a tachycardia event is not occurring and postpone delivery of shock therapy, declare MVT diagnosis, inhibit tachycardia therapy, etc.

FIG. 5B illustrates sensed peak amplitude, RR interval, and sense-to-peak duration clustering of oversensed P-waves. Left vertical axis 550 plots ECG trace 552 in millivolts, horizontal axis 554 plots time in seconds, and right vertical axis 556 plots RR intervals in milliseconds. R-wave peak amplitudes 558*a*-558*d* (not all are separately indicated) cluster to about −0.72 mV (e.g., indicated with cluster 570), while oversensed R-wave amplitudes 560*a*-560*d* (not all are separately indicated), which are associated with oversensed P-waves, cluster to about 0.41 mV (e.g., indicated with cluster 572). RR intervals 562*a*-562*d* (not all are separately indicated), which are associated with oversensed R-wave-to-P-wave (RP) intervals cluster to around 550 msec (e.g., indicated with cluster 574). RR intervals 564*a*-564*d* (not all are separately indicated), which are associated with oversensed P-wave-to-R-wave (PR) intervals, cluster to around 162 msec (e.g., indicated with cluster 576). However, in this example a true RR interval rate is about 715 msec. Sense-to-peak durations 566*a*-566*d* (not all are separately indicated) cluster to about 12 msec (e.g., true QRS with short sense-to-peak duration), and oversensed sense-to-peak durations 568*a*-568*d* (not all are separately indicated) cluster to about 132 msec (e.g., oversensed P-wave). The identification of the two distinct clusters associated with one or more of the correlation scores, sensed peak amplitude, RR interval, and sense-to-peak duration can be used to determine that a tachycardia event is not occurring and inhibit tachycardia therapy (e.g., shock therapy).

It should be understood that clustering methods and patterns of ECG characteristics as described herein can be used to identify QRS double sensing, P-wave oversensing, and/or T-wave oversensing.

Figure 5C:
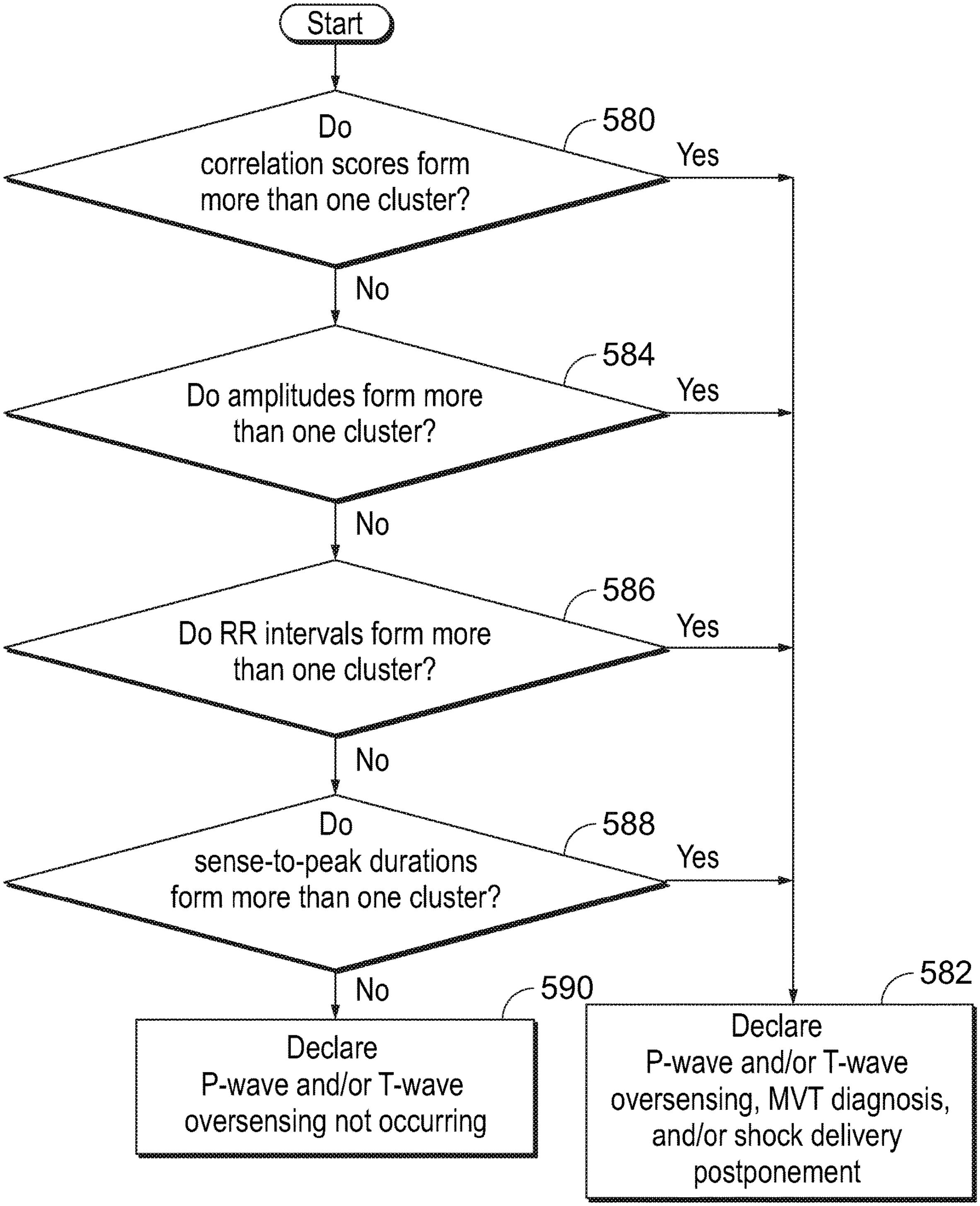
FIG. 5C illustrates a process for determining if oversensing of P-waves and/or T-waves is occurring such that tachycardia therapy (e.g., anti-tachycardia pacing or defibrillation shock) should be postponed and/or inhibited in accordance with embodiments herein.

FIG. 5C illustrates a process for determining if oversensing of P-waves and/or T-waves is occurring such that tachycardia therapy (e.g., anti-tachycardia pacing or defibrillation shock) should be inhibited and/or delayed in accordance with embodiments herein. The operations of FIG. 5C may be implemented by hardware, firmware, circuitry and/or one or more processors housed partially and/or entirely within an IMD, a local external device, remote server or more generally within a healthcare system. Optionally, the operations of FIG. 5C may be partially implemented by an IMD and partially implemented by a local external device, remote server or more generally within a healthcare system. For example, the IMD includes IMD memory and one or more IMD processors, while each of the external devices/systems (e.g., local, remote, or anywhere within the healthcare system) include external device memory and one or more external device processors. In some embodiments, the methods described herein can all or partly be performed by firmware, software, hardware, etc., on a beat-by-beat basis or on-demand using buffered data.

At 580, the one or more processors determine if correlation scores of the R-waves form more than one cluster. If more than one cluster is formed as discussed previously, RR oversensing can be occurring and the process passes to 582, where the one or more processors can declare P-wave and/or T-wave oversensing, postpone shock delivery, declare shock delivery postponement, declare MVT diagnosis, inhibit tachycardia therapy and/or accomplish further processing and analysis. If one cluster is identified, the process passes to 584. In other embodiments, the one or more processors can determine that P-wave and/or T-wave oversensing is occurring after additional conditions are met, such as one or more of 584, 586, and 588 discussed below. In some embodiments, one, two, or more of any combination of the conditions of 580, 584, 586, and 588 can be used to identify P-wave and/or T-wave oversensing and inhibit tachycardia therapy.

At 584 the one or more processors determine if amplitudes of the signal form more than one cluster. For example, R-wave peak amplitudes 558 and oversensed R-wave amplitudes 560 form separate and distinct clusters as discussed above. If more than one cluster is identified, the process can pass to 582. If one cluster is identified, the process passes to 586 where the one or more processors determine if RR intervals form more than one cluster. For example, the RR intervals 562 (e.g., oversensed RP intervals) and the RR intervals 564 (oversensed PR intervals) form separate and distinct clusters. If more than one cluster is identified, the process can pass to 582. If one cluster is identified, the process passes to 588 and the one or more processors determine if sense-to-peak durations form separate and distinct clusters. If more than one cluster is identified, the process passes to 582. If one cluster is identified, the process passes to 590 and the one or more processors determine that P-wave and/or T-wave oversensing is not occurring.

The embodiments herein are an improvement to the technology of IMDs 100, and in particular, to implantable cardiac devices in the technical field of cardiac shock therapy treatment and monitoring. The IMDs 100 continuously monitor a patient's cardiac signals and provide shock therapy, pacing, etc., as needed to maintain the function of the heart and prevent death and/or unnecessary treatment.

Further, the IMD 100 delivers the particular treatment and prophylaxis for the medical condition of arrhythmia (e.g., MVT, SVT, PVT, etc.). The candidate arrhythmia is confirmed before treatment is administered to the patient. For example, cardiac activity data collected by the IMD 100 can be used to confirm that an arrhythmia exists and to determine whether the arrhythmia requires treatment. Therefore, the level of treatment to be administered to the patient can be determined, such as no treatment, delay in treatment, pacing therapy, high-level shock treatment (e.g., shock therapy delivery), etc. As discussed in FIGS. 2A-3C, the IMD 100 monitors the FF signals and compares the signals to one or more templates to determine correlation scores. The correlation scores, along with other measurements such as amplitude, RR interval, and QRS duration are evaluated to ensure that the patient is treated when necessary, but is not subjected to unnecessary shock therapy delivery. As described further above, shock therapy delivery is quite painful and distressing to a patient if delivered unnecessarily, which may lead to patient non-compliance and poor outcomes.

Further, treatment and prophylaxis of the medical condition of arrhythmia is also discussed in FIGS. 4A-5C. The IMD 100 determines whether oversensing of R-waves, P-waves, and/or T-waves is occurring based on the FF signals. Oversensing can cause the FF signals to appear to be representative of an arrhythmia, and thus result in unnecessary treatment. By detecting oversensing, appropriate treatment can be delivered to the patient, improving both compliance and patient outcomes.

External Device

Figure 6:
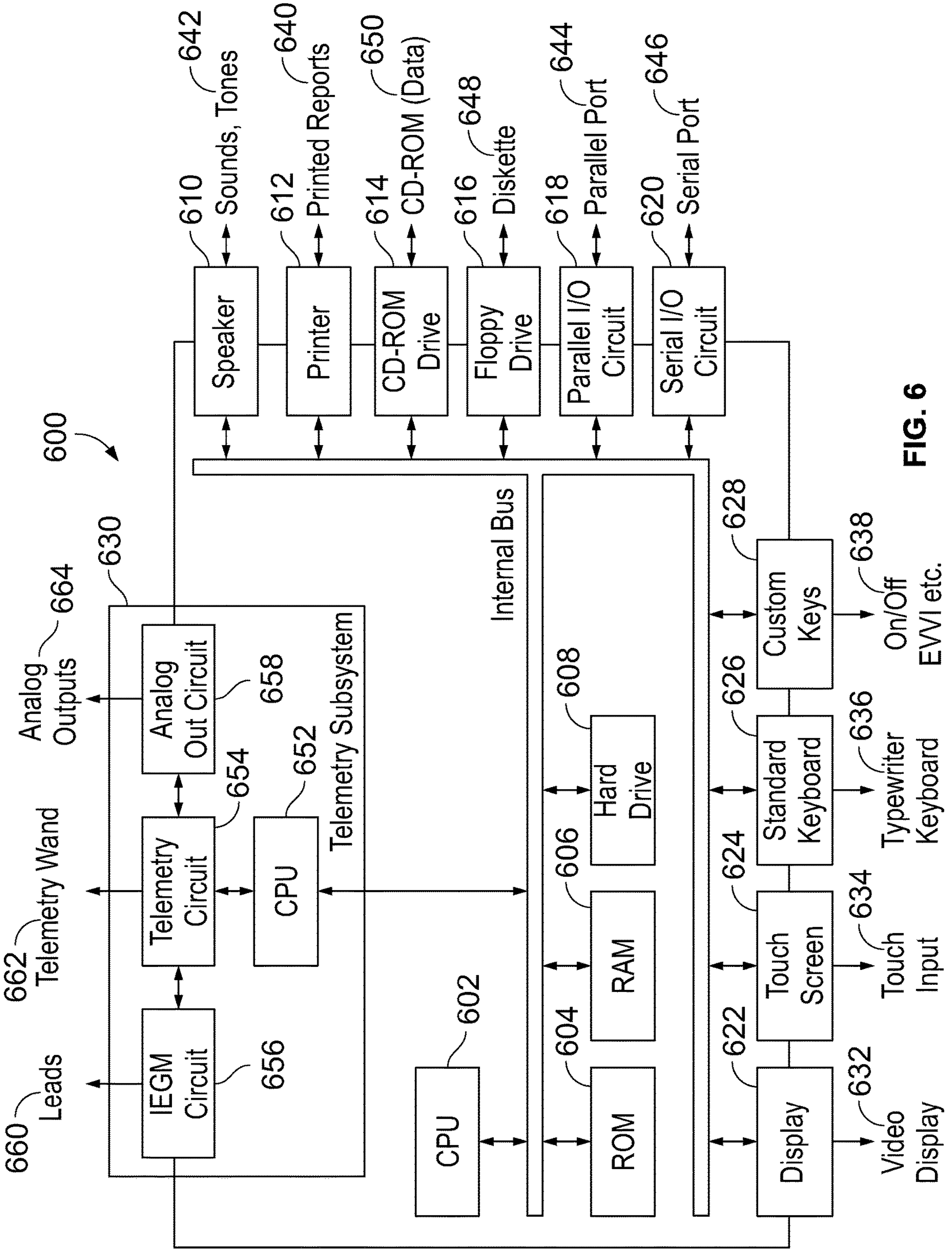
FIG. 6 illustrates a functional block diagram of the external device that is operated in accordance with the processes described herein and to interface with implantable medical devices as described herein.

FIG. 6 illustrates a functional block diagram of the external device 600 that is operated in accordance with the processes described herein and to interface with implantable medical devices as described herein. The external device 600 may be a workstation, a portable computer, an IMD programmer, a PDA, a cell phone, and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates (e.g., sinus QRS templates) and detection and discrimination algorithms and thresholds.

The CPU 602 typically includes a microprocessor, a micro-controller, or equivalent control circuitry, designed specifically to control interfacing with the external device 600 and with the IMD 100. The CPU 602 performs operations discussed herein in connection with FIGS. 2A-5C. The CPU 602 may include RAM or ROM memory, logic and timing circuitry, state machine circuitry, and I/O circuitry to interface with the IMD 100. The display 622 may be connected to the video display 632. The touch screen 624 may display graphic information relating to the IMD 100. The display 622 displays various information related to the processes described herein. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 includes a central processing unit (CPU) 652 in electrical communication with a telemetry circuit 654, which communicates with both an IEGM circuit 656 and an analog out circuit 658. The circuit 656 may be connected to leads 660. The circuit 656 is also connected to the implantable leads to receive and process IEGM cardiac signals as discussed above. Optionally, the IEGM cardiac signals sensed by the leads may be collected by the IMD 100 and then transmitted to the external device 600, such as wirelessly to the telemetry subsystem 630 input.

The telemetry circuit 654 is connected to a telemetry wand 662. The analog out circuit 658 includes communication circuits to communicate with analog outputs 664. The external device 600 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 600 to the IMD 100.

Implantable Medical Device

Figure 7:
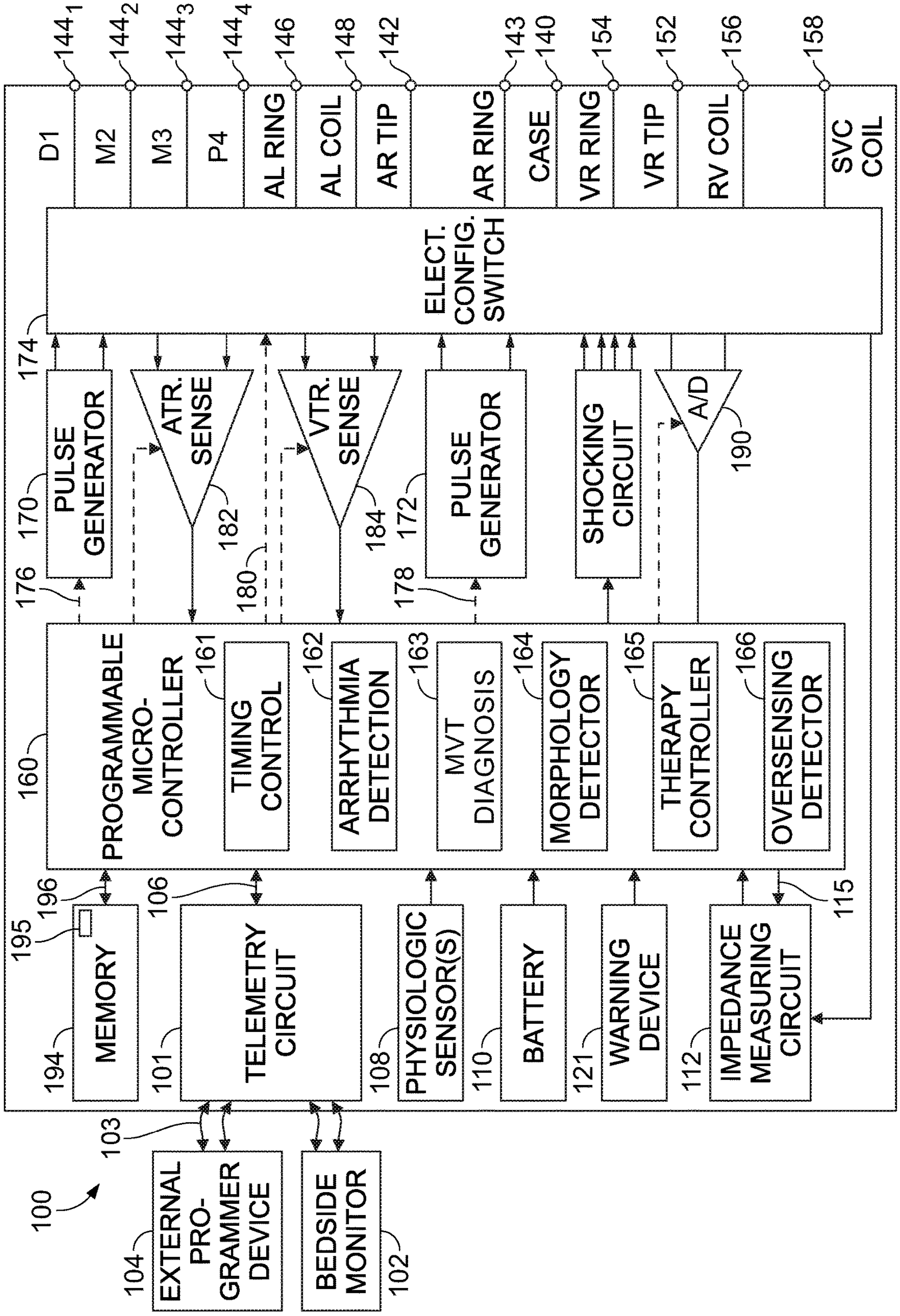
FIG. 7 illustrates a simplified block diagram of internal components of the IMD in accordance with embodiments herein.

FIG. 7 illustrates a simplified block diagram of internal components of the IMD 100 in accordance with embodiments herein. While a particular IMD 100 is shown, it is for illustration purposes only. One of skill in the art could readily duplicate, eliminate, or disable the appropriate circuitry in any desired combination to provide a device capable of treating the appropriate chamber(s) with cardioversion, defibrillation, and pacing stimulation. The housing/CAN 140 for IMD 100 may be programmably selected to act as the anode for at least some unipolar modes. The CAN 140 may further be used as a return electrode alone or in combination with one or more of the coil electrodes 128, 136, and 138 (all shown in FIG. 1) for shocking purposes.

The IMD 100 further includes a connector (not shown) having a plurality of terminals, 142, 143, $144_1$-$144_4$, 146, 148, 152, 154, 156, and 158 (shown schematically and, for convenience, with the names of the electrodes to which they are connected). As such, to achieve right atrial (RA) sensing and pacing, the connector includes at least an RA tip terminal ($A_R$ TIP) 142 adapted for connection to the atrial tip electrode 122 (shown in FIG. 1) and an RA ring ($A_R$ RING) electrode 143 adapted for connection to the RA ring electrode 123 (shown in FIG. 1). To achieve left chamber sensing, pacing, and shocking, the connector includes an LV tip terminal $144_1$adapted for connection to the D1 electrode and additional LV electrode terminals $144_2$, $144_3$, and $144_4$adapted for connection to the M2, M3, and P4 electrodes, respectively, of the quadripolar LV lead 124 (shown in FIG. 1). The connector also includes an LA ring terminal ($A_L$ RING) 146 and an LA shocking terminal ($A_L$ COIL) 148, which are adapted for connection to the LA ring electrode 127 (shown in FIG. 1) and the LA coil electrode 128 (shown in FIG. 1), respectively. To support right chamber sensing, pacing, and shocking, the connector further includes an RV tip terminal ($V_R$ TIP) 152, an RV ring terminal ($V_R$ RING) 154, an RV coil terminal (RV COIL) 156, and an SVC coil terminal (SVC COIL) 158, which are adapted for connection to the RV tip electrode 132, the RV ring electrode 134, the RV coil electrode 136, and the SVC coil electrode 138 (all four electrodes shown in FIG. 1), respectively.

The IMD 100 includes a programmable microcontroller 160 (also referred to herein as a control unit or controller) that includes a microprocessor or equivalent control circuitry, designed specifically for controlling the delivery of stimulation therapy. The microcontroller 160 may further include RAM or ROM memory, logic and timing circuitry, state machine circuitry, and/or I/O circuitry. The microcontroller 160 includes the ability to process or monitor input signals (data) as controlled by a program code stored in a designated block of memory. The details of the design and operation of the microcontroller 160 are not critical to the invention. Rather, any suitable microcontroller 160 may be used that carries out the functions described herein. Among other things, the microcontroller 160 receives, processes, and manages storage of digitized cardiac data sets from the various sensors and electrodes.

A pulse generator 170 and a pulse generator 172 are configured to generate and deliver a pacing pulse from at least one RV or RA pacing site, such as at one or more pacing sites along the RA lead 120, the RV lead 130, and/or the LV lead 124 (all three leads shown in FIG. 1). The pulse generators 170, 172 are controlled by the microcontroller 160 via appropriate control signals 176, 178, respectively, to trigger or inhibit the stimulation pulses, including the timing and output of the pulses. The electrode configuration switch 174 may include a plurality of switches for connecting the desired electrodes to the appropriate I/O circuits, thereby providing complete electrode programmability. Accordingly, the switch 174, in response to a control signal 180 from the microcontroller 160, controls the polarity of the stimulation pulses (e.g., unipolar, bipolar, etc.) by selectively actuating the appropriate combination of switches (not shown) as is known in the art. The switch 174 also switches among the various LV electrodes 126 to select the channels (e.g., vectors) to deliver and/or sense one or more of the pacing pulses. As explained herein, the switch 174 couples multiple LV electrode terminals $144_1$-$144_4$ correspond to cathodes when connected to the pulse generator 172.

Atrial sensors or sensing circuits 182 (e.g., sensing circuitry) and ventricular sensors or sensing circuits 184 (e.g., sensing circuitry) may also be selectively coupled to the RA lead 120, the LV lead 124, and/or the RV lead 130 (all three leads shown in FIG. 1) through the switch 174. The atrial and ventricular sensors 182 and 184 have the ability to detect the presence of cardiac activity in each of the four chambers of the heart 105 (shown in FIG. 1). For example, the ventricular sensor 184 is configured to sense LV activation events at multiple LV sensing sites, where the activation events are generated in response to a pacing pulse or an intrinsic event. In an embodiment, the ventricular sensor 184 senses along at least four sensing vectors, each sensing vector utilizing a sensing electrode in the left ventricle.

The atrial sensing circuits 182 and ventricular sensing circuits 184 are coupled to a lead, the lead having electrodes to sense near field (NF) and far field (FF) signals between first and second combinations of electrodes. The atrial sensing circuits 182 and ventricular sensing circuits 184 may include dedicated sense amplifiers, multiplexed amplifiers, or shared amplifiers. The switch 174 determines the "sensing polarity" or sensing vector of the cardiac signal by selectively opening and/or closing the appropriate switches, as is known in the art. In this way, a clinician may program the sensing polarity independent of the stimulation polarity.

Cardiac signals are also applied to the inputs of an analog-to-digital (A/D) data acquisition system 190. The A/D data acquisition system 190 is configured to acquire intracardiac electrogram (EGM) signals, convert the raw analog data into a digital signal, and store the digital signals for later processing and/or telemetric transmission. The telemetric transmission may be to an external programmer device 104, a bedside monitor 102, cellular phone, tablet device and/or a personal advisory module (PAM). The data acquisition system 190 may be operatively coupled to the RA lead 120, the LV lead 124, and the RV lead 130 (all three leads shown in FIG. 1) through the switch 174 to sample cardiac signals across any pair of desired electrodes.

The microcontroller 160 includes timing control module 161 to control the timing of the stimulation pacing pulses, including, but not limited to, pacing rate, atrio-ventricular delay, interatrial conduction delay, interventricular conduction delay, and/or intraventricular delay. The timing control module 161 can also keep track of the timing of refractory periods, blanking intervals, noise detection windows, evoked response detection windows, alert intervals, marker channel timing, etc., which is known in the art.

The microcontroller 160 further includes an arrhythmia detector 162 for operating the system as an implantable cardioverter/defibrillator device. The detector 162 applies arrhythmia detection algorithm(s) to the FF and NF signals for identifying events within the FF and NF signals. The detector 162 determines desirable times to administer various therapies. For example, the detector 162 may detect the occurrence of an arrhythmia and automatically control the application of, or inhibit the application of, an appropriate electrical shock therapy (e.g., shock therapy delivery) to the heart aimed at terminating the detected arrhythmia.

The microcontroller 160 includes a therapy controller 165 to manage pacing therapy, which can be performed in conjunction with CRT pacing. As an example, the therapy controller 165 may control the pulse generator 172 to simultaneously deliver a pacing pulse over a select pacing vector. The arrhythmia detector 162, morphology detector 164, and/or therapy controller 165 may be implemented in hardware as part of the microcontroller 160, or as software/firmware instructions programmed into the system and executed on the microcontroller 160 during certain modes of operation. The therapy controller 165 also controls delivery of CRT pacing pulses to synchronize the contractions of the right and left ventricles. The therapy controller 165 controls the number, timing, and output of the CRT pacing pulses delivered during each cardiac cycle, as well as over which pacing vectors the pacing pulses are to be delivered.

The morphology detector/discriminator 164 can determine correlation scores by comparing the FF signals associated with acquired beats to one or more stored templates (e.g., sinus QRS template 195).

The microcontroller 160 may additionally include an MVT diagnosis detector 163 that performs the operations described herein. The MVT diagnosis detector 163 determines correlation scores by comparing the FF signals associated with a number of beats to a template, such as one of the templates 195 that has been acquired using the same set of electrodes. The MVT diagnosis detector 163 compares the correlation scores of the number of beats to a correlation variability threshold and determines correlation variability scores for the number of beats. The MVT diagnosis detector 163 can postpone shock delivery, declare shock delivery postponement, inhibit shock therapy delivery and/or declare an MVT diagnosis in response to i) a first number of beats within the number of beats having the correlation scores that are less than the correlation variability threshold, and ii) a second number of beats within the number of beats having correlation variability scores that are less than a correlation stability threshold. Optionally, the correlation variability threshold is i) an absolute value or ii) a percentage of a mean of the correlation scores. Optionally, wherein the template 195 is representative of a sinus QRS rhythm or atrial pacing, and is acquired using the combination of electrodes. Optionally, the MVT diagnosis detector 163 determines and compares the correlation scores and determines the correlation variability scores in response to a heart rate level exceeding a threshold. Optionally, the MVT diagnosis detector 163 declares a shockable diagnosis in response to i) the first number of beats within the number of beats having the correlation scores that are less than the correlation threshold, or ii) the second number of beats within the number of beats having correlation variability scores that are greater than a correlation variability threshold.

Optionally, the MVT diagnosis detector 163 compares the correlation scores of the number of beats to a first sinus template correlation condition, and in response to the comparison indicating that the number of beats indicate a ventricular tachycardia (VT), comparing the correlation scores of the number of beats to a second sinus template correlation condition, wherein the second sinus template correlation condition is a reduced level of correlation compared to the first sinus template correlation condition.

Optionally, the MVT diagnosis detector 163 further determines the correlation variability threshold by determining a mean or median based on the correlation scores of the number of beats, and compares an absolute difference of each of the number of beats to the mean or median to determine the number of beats having stable correlation scores. Optionally, the MVT diagnosis detector 163 determines an absolute mean of QRS-wave peak amplitudes of the number of beats, determines a peak amplitude stability score associated with a third number of beats within the number of beats, wherein the peak amplitude stability score includes a relative absolute deviation from the absolute mean of the QRS-wave peak amplitudes of the number of beats, and postpones shock delivery and/or declares shock delivery postponement further in response to i) determining that the absolute mean of the QRS-wave peak amplitudes of the number of beats is higher than a QRS-wave peak amplitude of the template multiplied by a factor, and ii) determining that the third number of beats have peak amplitude stability scores of less than a predetermined amplitude. Optionally, the MVT diagnosis detector 163 determines RR intervals associated with the number of beats, determines a mean associated with the RR intervals, compares a relative absolute difference of the RR intervals to the mean or median associated with the RR intervals, and postpones shock delivery and/or declares shock delivery postponement further in response to determining that a fourth number of beats within the number of beats have a relative absolute difference to the mean or median that is less than a heart rate stability threshold. Optionally, the MVT diagnosis detector 163 determines durations of QRS complexes associated with the number of beats, determines a mean associated with the durations of the QRS complexes, and postpones shock delivery and/or declares shock delivery postponement further in response to i) determining that a fifth number of beats within the number of beats have durations of the QRS complexes that are equal to a duration of a QRS complex associated with the template or greater than a first predetermined time duration, and ii) determining that a sixth number of beats within the number of beats have an absolute deviation from the mean associated with the durations of the QRS complexes that is less than a second predetermined time duration.

Optionally, the MVT diagnosis detector 163 is configured to postpone shock delivery, by the pulse generator 170, based on FF signals and/or NR signals. The postponing of the shock delivery can be further based on one or more of i) a comparison of a mean of absolute peak amplitudes of QRS-wave peaks of a plurality of recent beats to a first voltage threshold; ii) a comparison of absolute peak amplitudes of QRS-wave peaks of the plurality of recent beats to a second voltage threshold; iii) a comparison of a mean of an absolute difference of beat-to-beat peak amplitudes of the QRS-wave peaks of the plurality of recent beats to a third voltage threshold; or iv) a comparison of an absolute difference of the beat-to-beat peak amplitudes of the QRS-wave peaks of the plurality of recent beats to an amplitude stability threshold. Optionally, the MVT diagnosis detector 163 is further configured to declare the MVT diagnosis based on both the FF signals and the NF signals.

Optionally, the MVT diagnosis detector 163 is configured to declare an MVT diagnosis based on FF signals and/or NR signals. The MVT diagnosis can be further based on one or more of i) a comparison of beat-to-beat RR intervals of the plurality of recent beats to a heart rate threshold; ii) a comparison of a range of RR intervals to a heart rate range stability threshold, the range of the RR intervals based on the plurality of recent beats and excluding at least one of a highest value and a lowest value; iii) a comparison of a largest absolute beat-to-beat interval difference of the beat-to-beat RR intervals of the plurality of recent beats to the heart rate range stability threshold; or iv) a determination of a percentage of the RR intervals, of the plurality of recent beats, with absolute difference less than a heart stability threshold, wherein the percentage is compared to a predetermined percentage.

The microcontroller 160 may additionally include an oversensing detector 166 that performs the operations described herein. The oversensing detector 166, when executing program instructions, is configured to inhibit tachycardia therapy based on i) a determination that correlation scores of a plurality of recent beats form more than one cluster, wherein the recent beats are associated with the FF signals sensed between the set of the electrodes, ii) a determination that amplitudes of sensed R-waves within the plurality of recent beats form more than one cluster, iii) a determination that peak RR intervals form more than one cluster, or a determination that sense-to-peak durations form more than one cluster. Optionally, the oversensing detector 166, in response to determining that the correlation scores of the plurality of recent beats form one cluster, is further configured to declare that oversensing is not occurring. Optionally, the oversensing can be i) P-wave oversensing, ii) T-wave oversensing, or iii) QRS-wave oversensing.

The microcontroller 160 is further coupled to a memory 194 by a suitable data/address bus 196. The programmable operating parameters used by the microcontroller 160 are stored in the memory 194 and modified, as required, in order to customize the operation of IMD 100 to suit the needs of a particular patient. Such operating parameters define, for example, the amplitude or magnitude of the generated pacing pulses, wave shape, pulse duration, and/or vector (e.g., including electrode polarity) for the pacing pulses. Other pacing parameters may include base rate, rest rate, and/or circadian base rate. The memory 194 also stores conduction patterns or morphologies, such as one or more sinus QRS templates 195, as well as other data and information described herein. The memory 194 stores the NF and FF signals.

Optionally, the operating parameters of the implantable IMD 100 may be non-invasively programmed into the memory 194 through a telemetry circuit 101 in telemetric communication with an external programmer device 104 or a bedside monitor 102, such as a programmer, trans-telephonic transceiver, cellular phone, or a diagnostic system analyzer. The telemetry circuit 101 is activated by the microcontroller 160 through a control signal 106. The telemetry circuit 101 may allow IEGMs, conduction patterns, morphologies as well as other data and information described herein, and status information relating to the operation of IMD 100 (contained in the microcontroller 160 or the memory 194) to be sent to the external programmer device 104 and/or bedside monitor 102, and vice-versa, through an established communication link 103. An internal warning device 121 may be provided for generating perceptible warning signals to a patient and/or caregiver via vibration, voltage, sounds or other methods.

IMD 100 further includes an accelerometer, temperature, or other physiologic sensor 108. The physiologic sensor 108 is commonly referred to as a "rate-responsive" sensor because it may be used to adjust the pacing stimulation rate according to the exercise state (e.g., heart rate) of the patient. However, the physiologic sensor 108 may further be used to detect changes in cardiac output, changes in the physiological condition of the heart, and/or diurnal changes in activity (e.g., detecting sleep and wake states and arousal from sleep).

The IMD 100 additionally includes a battery 110, which provides operating power to all of the circuits therein. The makeup of the battery 110 may vary depending on the capabilities of IMD 100. If the system only provides low voltage therapy (e.g., for repetitive pacing pulses), a lithium iodine or lithium copper fluoride cell may be utilized. For a IMD that employs shocking therapy, the battery may be configured to be capable of operating at low current drains for long periods and then providing high-current pulses (for capacitor charging) when the patient requires a shock pulse or shock therapy delivery by shocking circuit 192. The battery 110 may also be configured to have a predictable discharge characteristic so that elective replacement time can be detected.

Optionally, the IMD 100 includes an impedance measuring circuit 112, which is enabled by the microcontroller 160 via a control signal 115. Uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 112 is coupled to the switch 174 so that any desired electrode may be used.

The above-described implantable medical device 100 was described as an exemplary IMD. One of ordinary skill in the art would understand that one or more embodiments herein may be used with alternative types of implantable devices. Accordingly, embodiments should not be limited to using only the above-described device 100.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module," or "system." Furthermore, aspects may take the form of a computer (device) program product embodied in one or more computer (device) readable storage media having computer (device) readable program code embodied thereon.

Any combination of one or more non-signal computer (device) readable media may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices, and program products according to various example embodiments. These program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system, comprising:

electrodes;

an implantable medical device (IMD) coupled to the electrodes, the IMD including sensing circuitry and a pulse generator configured to deliver shock therapy to a patient via the electrodes, the IMD configured to sense far field (FF) signals, utilizing the sensing circuitry, between the electrodes;

memory to store the FF signals and to store program instructions, the memory further storing at least first and second sinus QRS templates associated with a set of the electrodes, the first QRS template acquired at a different heart rate than the second QRS template; and one or more processors that, when executing the program instructions, are configured to declare an MVT diagnosis based on:

i) a first comparison of a plurality of recent beats to a selected one of the first or second sinus QRS templates for morphology discrimination after tachycardia entry criteria are met, the one or more processors configured to compare the first plurality of recent beats to the selected one of the first or second QRS templates by aligning the plurality of recent beats to the selected one of the first or second sinus QRS templates and performing a cross-correlation to determine correlation scores for the plurality of recent beats;

ii) a second comparison of the correlation scores of the plurality of recent beats to a correlation threshold, wherein the recent beats are based on the FF signals sensed between the electrodes in the set; and iii) a variability of the correlation scores of the plurality of recent beats being less than a correlation variability threshold, wherein the one or more processors are configured to direct the pulse generator to postpone delivery of the shock therapy responsive to declaring the MVT diagnosis.

2. The system of claim 1, wherein the MVT diagnosis is a first MVT diagnosis and, in response to the one or more processors declaring a second MVT diagnosis within a predetermined time of the first MVT diagnosis, the one or more processors are further configured to postpone delivery of the shock therapy a second time.

3. The system of claim 1, wherein the one or more processors are further configured to declare the MVT diagnosis based on a comparison of R-wave peak amplitudes of the plurality of recent beats to an R-wave peak amplitude associated with the sinus QRS template.

4. The system of claim 1, wherein the one or more processors are further configured to declare the MVT diagnosis based on a heart rate stability associated with the plurality of recent beats.

5. The system of claim 1, wherein the one or more processors are further configured to declare the MVT diagnosis based on i) a comparison of durations of QRS complexes associated with the plurality of recent beats to a duration of a QRS complex associated with the selected one of the first or second sinus QRS templates and ii) a stability of the durations of the QRS complexes associated with the plurality of recent beats.

6. The system of claim 1, wherein the set of electrodes is a first set of electrodes, and further comprising:

wherein the IMD is further configured to sense the FF signals, utilizing the sensing circuitry, between a second set of the electrodes, wherein at least one of the electrodes within the second set of the electrodes is different from one of the electrodes within the first set of the electrodes; and wherein the memory is further configured to store a second template associated with the second set of the electrodes.

7. A system, comprising:

implantable electrodes;

an implantable medical device (IMD) coupled to the electrodes, the IMD including sensing circuitry and a pulse generator, the IMD configured to sense far field (FF) signals, utilizing the sensing circuitry, between the electrodes;

memory to store the FF signals and to store program instructions, the memory further storing a sinus QRS template associated with a set of the electrodes; and one or more processors that, when executing the program instructions, are configured to postpone shock delivery, by the pulse generator, based on:

i) a first comparison of a plurality of recent beats to a sinus QRS template by aligning the recent beats to the sinus QRS template and performing a cross-correlation to determine correlation scores for the recent beats;

ii) a determination that the correlation scores of the plurality of recent beats form more than one cluster, wherein the recent beats are associated with the FF signals sensed between the electrodes in the set;

iii) a determination that amplitudes of sensed R-waves within the plurality of recent beats form more than one cluster;

iv) a determination that peak RR intervals form more than one cluster; or v) a determination that sense-to-peak durations form more than one cluster, wherein the determination that the correlation scores form more than the one cluster, the determination that the amplitudes of the sensed R-form more than the one cluster, the determination that the peak RR intervals form more than the one cluster, or the determination that the sense-to-peak durations form more than the one cluster includes identifying a multiple cluster pattern by:

separating metric values of the recent beats into a smallest half of the metric values and a largest half of the metric values;

determining means or medians for each of the smallest half of the metric values and the largest half of the metric values; and determining that the metric values within each of the smallest half and the largest half remain within a corresponding deviation threshold of the mean or median of the respective smallest half or the largest half.

8. The system of claim 7, wherein the one or more processors, in response to determining that the correlation scores of the plurality of recent beats form more than one cluster, is further configured to declare that oversensing is occurring.

9. The system of claim 8, wherein the oversensing is i) P-wave oversensing, ii) T-wave oversensing, or iii) QRS-wave oversensing.

10. A system, comprising:

electrodes;

an implantable medical device (IMD) coupled to the electrodes, the IMD including sensing circuitry and a pulse generator, the IMD configured to sense far field (FF) signals and near field (NF) signals, utilizing the sensing circuitry, between the electrodes;

memory to store the FF signals and the NF signals and to store program instructions; and a processor that, when executing the program instructions, is configured to postpone shock delivery, by the pulse generator, based on the FF signals or the NF signals, wherein the postponing the shock delivery is further based on:

i) a comparison of a mean of absolute peak amplitudes of QRS-wave peaks of a plurality of recent beats to a first voltage threshold;

ii) a comparison of absolute peak amplitudes of the QRS-wave peaks of the plurality of recent beats to a second voltage threshold;

iii) a comparison of a mean of an absolute difference of beat-to-beat peak amplitudes of the QRS-wave peaks of the plurality of recent beats to a third voltage threshold;

iv) a comparison of an absolute difference of the beat-to-beat peak amplitudes of the QRS-wave peaks of the plurality of recent beats to an amplitude stability threshold;

v) a comparison of beat-to-beat RR intervals of the plurality of recent beats to a heart rate threshold;

vi) a comparison of a range of RR intervals to a heart rate range stability threshold, the range of the RR intervals based on the plurality of recent beats and excluding at least one of a highest value and a lowest value;

vii) a comparison of a largest absolute beat-to-beat interval difference of the beat-to-beat RR intervals of the plurality of recent beats to the heart rate range stability threshold; or viii) a determination of a percentage of the RR intervals, of the plurality of recent beats, with an absolute difference less than a heart stability threshold, wherein the percentage is compared to a predetermined percentage.

11. The system of claim 10, wherein the postponing the shock delivery is further based on both the FF signals and the NF signals.

* * * * *